(12) United States Patent
Sakuma et al.

(10) Patent No.: US 9,023,398 B2
(45) Date of Patent: May 5, 2015

(54) METHOD FOR IMPROVING THE AQUEOUS SOLUBILITY OF POORLY-SOLUBLE SUBSTANCES

(75) Inventors: Shuji Sakuma, Tokyo (JP); Keiichiro Kikukawa, Tokyo (JP); Ryosuke Miyasaka, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 0 days.

(21) Appl. No.: 13/497,637

(22) PCT Filed: Sep. 10, 2010

(86) PCT No.: PCT/JP2010/005545
§ 371 (c)(1),
(2), (4) Date: Jun. 29, 2012

(87) PCT Pub. No.: WO2011/039952
PCT Pub. Date: Apr. 7, 2011

(65) Prior Publication Data
US 2012/0264608 A1  Oct. 18, 2012

(30) Foreign Application Priority Data

Sep. 30, 2009 (JP) ................................ 2009-226130

(51) Int. Cl.
| | |
|---|---|
| *A61K 9/14* | (2006.01) |
| *A01N 25/26* | (2006.01) |
| *A61K 47/02* | (2006.01) |
| *A23L 1/00* | (2006.01) |
| *A01N 25/08* | (2006.01) |

(Continued)

(52) U.S. Cl.
CPC ............... *A23L 1/0047* (2013.01); *A01N 25/08* (2013.01); *A01N 25/26* (2013.01); *A23L 1/0305* (2013.01); *A61K 9/501* (2013.01); *A61K 9/5015* (2013.01)

(58) Field of Classification Search
None
See application file for complete search history.

(56) References Cited

U.S. PATENT DOCUMENTS

| 3,966,899 A | 6/1976 | Nakai et al. |
| 4,859,471 A | 8/1989 | Fulberth et al. |

(Continued)

FOREIGN PATENT DOCUMENTS

| EP | 1072650 | 1/2001 |
| JP | 51-32719 | 3/1976 |

(Continued)

OTHER PUBLICATIONS

English machine translation dated Apr. 4, 2013 of Uchiyama et al., JP2000095655A, published Apr. 4, 2000.*

(Continued)

*Primary Examiner* — Michael B Pallay
(74) *Attorney, Agent, or Firm* — Kenneth H. Sonnenfeld; Margaret B. Brivanlou; King & Spalding LLP

(57) ABSTRACT

Provided is a method for increasing the solubility of a poorly-soluble substance used in pharmaceutical products, veterinary pharmaceutical products, quasi-drugs, cosmetic products, food products, agricultural chemicals, and the like, without using large amounts of additives. This is a method for improving aqueous solubility, which comprises coating the surface of the particle of a poorly-soluble substance used in pharmaceutical products, veterinary pharmaceutical products, quasi-drugs, cosmetic products, food products, agricultural chemicals, and the like, with microparticles of a calcium compound such as calcium phosphate or calcium carbonate.

11 Claims, 10 Drawing Sheets

(51) Int. Cl.
*A23L 1/03* (2006.01)
*A61K 9/50* (2006.01)

(56) References Cited

U.S. PATENT DOCUMENTS

| | | | |
|---|---|---|---|
| 5,122,418 A * | 6/1992 | Nakane et al. | 424/401 |
| 2003/0162287 A1 * | 8/2003 | Yamamoto et al. | 435/289.1 |
| 2006/0153913 A1 | 7/2006 | Yamane et al. | |
| 2007/0243260 A1 | 10/2007 | Snape et al. | |

FOREIGN PATENT DOCUMENTS

| | | | | |
|---|---|---|---|---|
| JP | 61-145124 | | 7/1986 | |
| JP | 04-308513 | | 10/1992 | |
| JP | 05-032524 | | 2/1993 | |
| JP | 05-178765 | | 7/1993 | |
| JP | 05-271066 | | 10/1993 | |
| JP | 07-304633 | | 11/1995 | |
| JP | 07-328416 | | 12/1995 | |
| JP | 08-301763 | | 11/1996 | |
| JP | 2642486 | | 5/1997 | |
| JP | 10-025255 | | 1/1998 | |
| JP | 2000-095655 | | 4/2000 | |
| JP | 2000-95655 | | 4/2000 | |
| JP | 2000095655 A * | 4/2000 | | A61K 7/16 |
| JP | 2001-098185 | | 4/2001 | |
| JP | 2001098185 A * | 4/2001 | | C09C 3/06 |
| JP | 2002-519316 | | 7/2002 | |
| JP | 2003-104911 | | 4/2003 | |
| JP | 2006-016392 | | 1/2006 | |
| JP | 2006-131709 | | 5/2006 | |
| JP | 2007-176869 | | 7/2007 | |
| JP | 2007-536362 | | 12/2007 | |
| JP | 2008-007479 | | 1/2008 | |
| JP | 2008-120757 | | 5/2008 | |
| WO | WO 00/00177 | | 1/2000 | |
| WO | WO 2005/018607 | | 3/2005 | |
| WO | WO 2005/037268 | | 4/2005 | |

OTHER PUBLICATIONS

Bermudez et al., "Pulmonary Responses of Mice, Rats, and Hamsters to Subchronic Inhalation of Ultrafine Titanium Dioxide Particles", 2004, Toxicological Sciences, vol. 77, No. 2, pp. 347-357.*

TOTAL Polystyrene Material Safety Data Sheet, 2009, Total Petrochemicals USA, Inc., pp. 1-6.*

English machine translation dated Aug. 11, 2013 of Noguchi et al. (JP 2001-98185 A; published Apr. 10, 2001), pp. 1-6.*

Occupational Health Guideline for Mica, Sep. 1978, U.S. Dep't. of Health and Human Services and U.S. Dep't. of Labor, pp. 1-4.*

Kabushiki Kaisha Sangi JP, Inquiry of Substantive Examination for Russian Patent Application No. 2012115189/15 dated May 21, 2013, 7 pages.

Colloid oyobi Kaimen Kagaku Bukai (Division of Colloid and Surface Chemistry), Dai 23-kai Gendai Colloid Kaimen Kagaku Kiser Koza Youshi (The 23rd Modern Colloid and Surface Chemistry Basic Course, Abstract), "Iyaku Kaihatsu ni okeru Kaimenkassel-zai no Jyuyousei (Importance of surfactants in development of pharmaceutical products)".

Kabushiki Kaisha Sangi, International Search Report for PCT/JP2010/005545, dated Oct. 19, 2010, 8 pages.

Kohsaku Kawakami, "Importance of Surface Chemistry in the Development of Pharmaceutical Products," *Division of Colloid and Surface Chemistry, The 23rd Modern Colloid and Surface Chemistry Basic Course*, May 16-18, 2007, 17 pages.

* cited by examiner

METHOD FOR IMPROVING THE AQUEOUS SOLUBILITY OF POORLY-SOLUBLE SUBSTANCES

TECHNICAL FIELD

The present invention relates to a method for improving the aqueous solubility of a poorly-soluble substance used in pharmaceutical products, veterinary pharmaceutical products, quasi-drugs, cosmetic products, food products, agricultural chemicals, and the like.

BACKGROUND ART

Useful substances have often poor solubility in water in the fields of pharmaceutical products, veterinary pharmaceutical products, quasi-drugs, cosmetic products, food products, agricultural chemicals, and the like. This restricts the use of useful substances. In general, as methods for increasing the solubility of poorly-soluble drugs or increasing the dissolution rate thereof, a method involving mechanical microparticulation, a method in which such a poorly-soluble drug is included with cyclodextrin or the like, a method in which the solubility of such a poorly-soluble drug is increased using a surfactant or a solubilizer, and the like have been adopted.

There are various types of methods for administering pharmaceutical products, such as oral administration, intravenous administration, intramuscular administration, subcutaneous administration, transdermal administration, transnasal administration, and pulmonary administration. In the case of oral administration, for example, in order that an orally administered drug effectively acts on a living body, first of all, the drug must be disintegrated, dissolved and absorbed into the body. When the drug used has extremely low solubility in water, the blood concentration of the drug becomes low, and as a result, an entire amount of the drug is not absorbed and a portion of the drug is eliminated from the body in the undissolved form. Thus, expected drug effects may not be obtained in some cases. In addition, in the case of cutaneous administration, a drug cannot be sufficiently absorbed transdermally when poorly-soluble powder is merely incorporated into an ointment or a patch base such as a poultice. Thus, such a poorly-soluble drug in a dissolved state must be mixed into the base. In many cases, such a poorly-soluble drug must be mixed into alcohols at a high concentration, and thus, it is unfavorable in terms of skin safety. Moreover, in the case of intravenous administration, when a drug to be administered has low solubility, it is difficult to administer the drug by intravenous administration. In all of these administration methods, the solubility of a drug to be administered is associated with retardation of the time at which an effective blood concentration is achieved or a decrease in biological availability. Hence, the solubility of a drug has great influence on the effects of the drug.

Furthermore, in the case of a whitening ingredient used in cosmetic products, its effect is expressed as a result of penetration into the skin. Accordingly, it is important to improve the transdermal absorbency of the whitening ingredient. Thus, it is necessary that the solubility of a poorly-soluble substance be increased and that the transdermal absorbency thereof be improved.

Further, in the case of an agricultural chemical that is poorly soluble in water, it is slowly dissolved, and sufficient drug effects cannot be achieved in some cases. Accordingly, in the case of a granular agricultural chemical containing a poorly water-soluble ingredient as an active ingredient, promotion of dissolution of the active ingredient is important. As insecticidal ingredients, there are many poorly water-soluble drugs. When a pharmaceutical preparation such as a liquid preparation is produced, a kerosene-type solvent is often used because of usability such as odor or stimulation, low toxicity, high safety due to a high flash point, as well as compatibility with insecticidal ingredients. The solubility of such insecticidal ingredients is generally low. On the other hand, these ingredients have high solubility in solvents such as acetone, toluene, xylene and chloroform. However, these solvents have a low flash point, high toxicity, and strong odor. Thus, they are generally impractical.

Hence, the improvement of the solubility of a poorly-soluble drug is extremely important in the fields of pharmaceutical products, veterinary pharmaceutical products, quasi-drugs, cosmetic products, food products, agricultural chemicals, and the like.

Under the aforementioned circumstances, a large number of methods have been proposed, such as a method in which the surface area of a poorly-soluble drug is increased by microparticulation, a method in which such a poorly-soluble drug is included in cyclodextrin or the like, a method in which such a poorly-soluble drug is converted into an amorphous form, a method in which pH is adjusted, and a method in which the solubility of such a poorly-soluble drug is increased using a solubilizer or an organic solvent. Moreover, at present, nano-level microparticulation technology has attracted attention. This is a micellisation technology or a technology using surfactants. The technology using surfactants is a most commonly used technique.

For example, the following methods have been disclosed: a method, which comprises mixing a poorly-soluble drug with sugar or sugar alcohol, and then subjecting the mixture to high-speed stirring grinding or impact grinding to obtain ultrafine particles, so as to increase the surface area of drug particles and to enhance the dissolution rate of the drug due to water solubility and dispersibility of the sugars (see Patent Document 1); a method, which comprises dissolving or suspending a poorly-soluble drug and a polymeric carrier such as hydroxylpropyl methyl cellulose or polyvinyl pyrrolidone in a mixed solution of water and an organic solvent such as alcohol, and then grinding and drying it by pulse combustion drying to obtain spherical fine particles of the poorly-soluble drug and the polymeric carrier, so as to increase the surface area of the drug particles and to thereby enhance the dissolution rate of the drug (see Patent Document 2); a method in which a poorly-soluble drug is included in cyclodextrin, a derivative thereof or the like to improve the solubility of the drug (see Patent Document 3); a method in which a poorly-soluble drug is grinded together with crystalline cellulose to convert it into an amorphous form, so as to increase the solubility of the drug (see Patent Document 4); a method, which comprises melting a poorly-soluble acidic drug or a salt thereof, and then mixing the resultant with a basic magnesium-containing compound to convert the acidic drug or the salt thereof to an amorphous form, so as to increase the solubility of the drug (see Patent Document 5); a method in which a fatty acid ester of 2-ethyl-2-butyl-1,3-propanediol is used as a solubilizer for a poorly-soluble drug (see Patent Document 6); a method, which comprises dissolving glycyrrhizinic acid and a poorly-soluble drug in an organic solvent or the like, and then distilling away the solvent, so as to increase the solubility of the drug and the dissolution rate thereof (Patent Document 7); a method of improving the solubility of a pharmaceutical preparation, which comprises dissolving a poorly-soluble drug having micelle formation ability in water to form a micelle, and then fixing the micellar structure formed in the poorly-soluble drug, using a compound for fixing such a micellar structure (Patent Document 8); and a method, which comprises dissolving a poorly water-soluble drug and one or two or more types of nonionic surfactants in a solvent, then mixing an inorganic carrier into the resultant, so that the poorly water-soluble drug and the nonionic surfactant(s) are adsorbed on the carrier, and then removing the solvent (see Patent Document 9).

The method involving the microparticulation of a drug is a most commonly used technique of improving the solubility of the drug. In reality, such a microparticulation range is up to approximately several micrometers, and thus, microparticulation does not contribute to an increase in the solubility so much. On the contrary, there may be a case in which the cohesiveness or adhesiveness of a drug is increased by microparticulation, a drug is consolidated, or the dissolution rate is decreased. In addition, in the method in which a drug is included in cyclodextrin or the like, a freeze-drying method or the like is generally used. This method includes a long production time and a large number of steps, and thus, it cannot be said that this method is advantageous in terms of industrialization. Moreover, in order to include a drug in cyclodextrin or the like, it is generally necessary to use cyclodextrin in the same amount as that of the drug. Hence, as the amount of such an additive increases, the amount of the drug also increases. Furthermore, in the case of the method in which a drug is converted into an amorphous form, such an amorphous form is inherently an unstable state, and it is easily converted to a crystalline state that is a stable form by an external stimulation such as light, heat or humidity, or with time. Hence, it is difficult to maintain an amorphous form. Further, in the case of the method of increasing the solubility of a poorly-soluble drug using a solubilizer, an organic solvent is generally used. Thus, there is a possibility that such an organic solvent remains in a pharmaceutical preparation, and it causes safety problem. Since a large amount of organic solvent should be recovered safely from the viewpoint of environmental preservation, it leads to high production costs, and this method is also problematic in terms of the health maintenance and safety of workers. Still further, in the case of the method using a surfactant, the amount of a surfactant that can be used in a pharmaceutical preparation is generally approximately several hundreds of milligrams, taking into consideration the toxicity of the surfactant. However, this amount is not sufficient for increasing solubility. On the other hand, if a sufficient amount of surfactant is used to increase solubility, such a large amount of surfactant causes great damage on the intestinal mucosa (see Non-Patent Document 1).

PRIOR ART DOCUMENTS

Patent Documents

Patent Document 1: Japanese Patent No. 2642486
Patent Document 2: Japanese unexamined Patent Application Publication No. 2007-176869
Patent Document 3: Japanese unexamined Patent Application Publication No. 5-178765
Patent Document 4: Japanese unexamined Patent Application Publication No. 51-32719
Patent Document 5: Japanese unexamined Patent Application Publication No. 5-271066
Patent Document 6: Japanese unexamined Patent Application Publication No. 2003-104911
Patent Document 7: Japanese unexamined Patent Application Publication No. 10-25255
Patent Document 8: WO2005/018607
Patent Document 9: Japanese unexamined Patent Application Publication No. 8-301763

Non-Patent Documents

Non-patent Document 1: Colloid oyobi Kaimen Kagaku Bukai (Division of Colloid and Surface Chemistry), Dai 23-kai Gendai Colloid Kaimen Kagaku Kiso Koza Youshi (The 23$^{rd}$ Modern Colloid and Surface Chemistry Basic Course, Abstract), "Iyaku Kaihatsu ni okeru Kaimen-kassei-zai no Jyuyousei (Importance of surfactants in development of pharmaceutical products)"

SUMMARY OF THE INVENTION

Object to be Solved by the Invention

As described above, it is not easy to dissolve a poorly-soluble substance in water. If the solubility of a poorly-soluble substance that has not previously been dissolved can be increased, the types of usable substances are increased, and the range of use is also extended. It is an object of the present invention to provide a method for increasing the solubility of a poorly-soluble substance used in pharmaceutical products, veterinary pharmaceutical products, quasi-drugs, cosmetic products, food products, agricultural chemicals, and the like, without using large amounts of additives.

Means to Solve the Object

In order to improve the solubility of a poorly-soluble substance, the present inventors have searched various additives and have conducted studies regarding modification of the particles of such a poorly-soluble substance, etc. As a result, the present inventors have found that the solubility of the poorly-soluble substance can be improved by coating the surface of the poorly-soluble substance particle with the microparticles of a calcium compound such as calcium phosphate or calcium carbonate, thereby completing the present invention. With regard to a mechanism of improving the solubility of a poorly-soluble substance by coating the surface of the poorly-soluble substance particle with the calcium compound microparticles, it is considered that the coating calcium compound microparticles give a wetting effect on the poorly-soluble substance, and that, when the microparticles are removed from the poorly-soluble substance and are then dispersed, they are removed in a state in which a portion of the poorly-soluble substance remains attached thereto, and that the dispersibility of the poorly-soluble substance is thereby improved, and the solubility thereof is also improved. Hereinafter, the surface of a poorly-soluble substance particle, which is coated with microparticles of calcium compound, is referred to as a substance with improved aqueous solubility.

Specifically, the present invention relates to: (1) a method for producing a substance with improved aqueous solubility, which comprises coating a surface of a poorly-soluble substance particle with calcium compound microparticles; (2) the method for producing a substance with improved aqueous solubility according to (1) above, wherein the calcium compound is calcium phosphate or calcium carbonate; (3) the method for producing a substance with improved aqueous solubility according to (2) above, wherein the calcium phosphate is hydroxyapatite or tricalcium phosphate; and (4) the method for producing a substance with improved aqueous solubility according to any one of (1) to (3) above, wherein at least 5% of the surface of the poorly-soluble substance particle is coated with the calcium compound microparticles.

Moreover, the present invention relates to: (5) the method for producing a substance with improved aqueous solubility according to any one of (1) to (4) above, wherein the surface of the poorly-soluble substance particle is coated by applying mechanical energy to allow the calcium compound microparticles to penetrate into the poorly-soluble substance particle; (6) the method for producing a substance with improved aqueous solubility according to (5) above, wherein the method of applying mechanical energy is a method involving mechanical fusion; (7) the method for producing a substance with improved aqueous solubility according to (5) above, wherein the method of applying mechanical energy is a method involving hybridization; (8) the method for producing a substance with improved aqueous solubility according to any one of (1) to (7) above, wherein a mean particle size of the calcium compound microparticles is 100 μm or less; (9) the method for producing a substance with improved aqueous solubility according to any one of (1) to (8) above, wherein the specific surface area of the calcium compound microparticles is 20 $m^2/g$ or more; (10) the method for producing a substance with improved aqueous solubility according to any one of (1) to (9) above, wherein the calcium compound microparticles are microparticles coated with a dispersing agent; (11) the method for producing a substance with improved aqueous solubility according to (10) above, wherein the dispersing agent is at least one selected from among citric acid, citrate, pyrophosphoric acid, and chondroitin sulfate; and (12) the method for producing a substance with improved aqueous solubility according to any one of (1) to (11) above, wherein the poorly-soluble substance is a substance acting as an active ingredient of any one of a pharmaceutical product, a veterinary pharmaceutical product, a quasi-drug, a cosmetic product and an agricultural chemical, or a food additive.

Furthermore, the present invention relates to: (13) a substance with improved aqueous solubility obtained by the method according to any one of (1) to (12) above; (14) a pharmaceutical product, a veterinary pharmaceutical product, a quasi-drug, a cosmetic product, an agricultural chemical or a food product, formulated with the substance with improved aqueous solubility according to (13) above; and (15) the pharmaceutical product, veterinary pharmaceutical product, quasi-drug, cosmetic product, agricultural chemical or food product according to (14) above, which is an aqueous liquid composition.

Effect of the Invention

According to the present invention, a poorly-soluble substance used in pharmaceutical products, veterinary pharmaceutical products, quasi-drugs, cosmetic products, food products, agricultural chemicals, and the like, can be dissolved in water at a solubility that is higher than the original solubility of the poorly-soluble substance, without using large amounts of additives. In addition, the present invention is advantageous in terms of productivity and cost performance, it is excellent in terms of safety for workers, and it is highly useful in industrial application.

MODE FOR CARRYING OUT THE INVENTION

Figure 1:
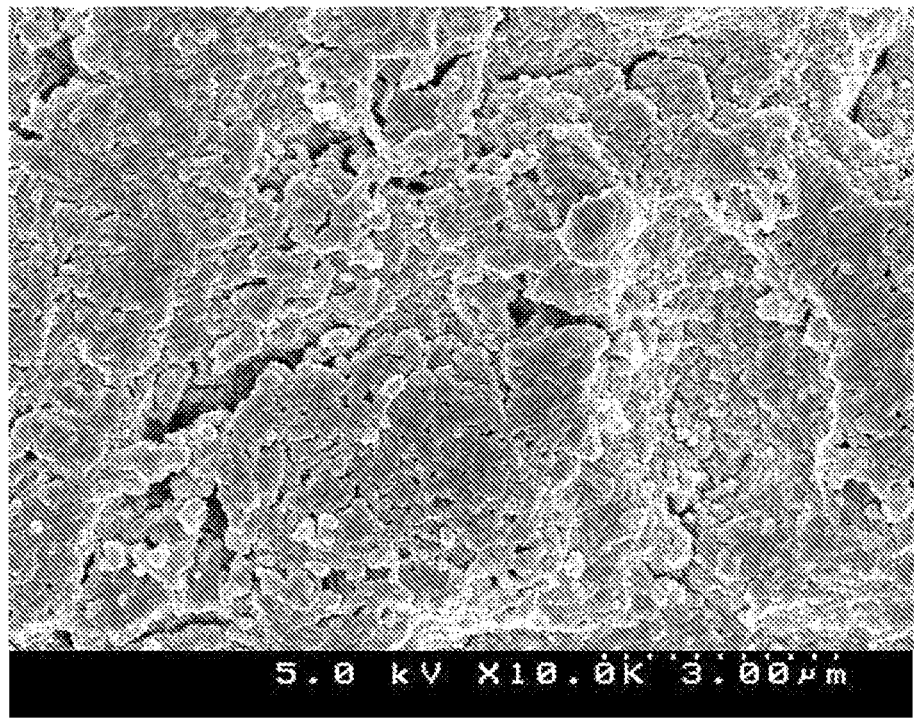
FIG. 1 shows an electron micrograph (10000-fold) of the aspirin of Example 1-1 that is 100% coated with hydroxyapatite.

The method of the present invention for producing a substance with improved aqueous solubility is not particularly limited, as long as it is a method in which the surface of a poorly-soluble substance particle is coated with microparticles of calcium compound. The term "dissolution" is used in the present invention to not only include a state in which a substance is completely dissolved in water, but also include a state in which a substance is uniformly dispersed in an aqueous medium and it seems a transparent liquid by visual observation, such as a solubilized state as a result of micelle formation or the like. It means a state in which the amount of a substance dissolved can be measured by a test method generally used in the measurement of the dissolved amount of such a substance.

The calcium compound is preferably a poorly-soluble calcium compound that is hardly dissolved in water. Examples of such a compound include calcium phosphate, calcium carbonate, calcium sulfate, and calcium hydroxide. Of these, calcium phosphate and calcium carbonate are preferable. These calcium compounds may be used singly or in the form of a mixture of two or more types.

An example of the calcium phosphate is a calcium phosphate having a Ca/P ratio of 0.8 to 2.0, and preferably having a Ca/P ratio of 1.0 to 2.0. Specific examples of such calcium phosphate include hydroxyapatite, tricalcium phosphate, tetracalcium phosphate, octacalcium phosphate, calcium hydrogen phosphate, calcium pyrophosphate, and calcium metaphosphate. Of these, hydroxyapatite and tricalcium phosphate are preferable. Moreover, the calcium phosphate may be obtained from the nature, or may also be synthesized by a known method such as a wet method or a dry method.

The hydroxyapatite is one type of calcium phosphate, which is a main ingredient of the bone. In general, it is shown as a stoichiometric composition represented by $Ca_{10}(PO_4)_6(OH)_2$. The hydroxyapatite is characterized in that it can exhibit properties as hydroxyapatite and can adopt an apatite structure even if it is a non-stoichiometric composition whose Ca/P molar ratio is not 1.67. In the present invention, both hydroxyapatite as a stoichiometric composition and hydroxyapatite as a non-stoichiometric composition can be used. Hydroxyapatite having a Ca/P molar ratio of 1.4 to 1.8 is preferably used.

In general, as methods for synthesizing hydroxyapatite, there are various types of synthetic methods such as dry synthesis and wet synthesis. In the case of the wet synthesis for example, hydroxyapatite can be obtained by allowing a calcium salt to react with phosphate in an aqueous solution. The Ca/P molar ratio of hydroxyapatite can be controlled by regulating the mixing ratio of a salt as a raw material or synthetic conditions. In the wet synthetic method for example, if an aqueous solution is adjusted to be basic using an ammonia water or the like during the synthesis, the Ca/P molar ratio can be controlled to be high. On the other hand, if the aqueous solution is adjusted to be neutral or weakly acidic using dilute acid, the Ca/P molar ratio can be controlled to be low.

The tricalcium phosphate may be either $\alpha$-$Ca_3(PO_4)_2$ or $\beta$-$Ca_3(PO_4)_2$. Of these, $\alpha$-$Ca_3(PO_4)_2$ is preferable because this is a more bioactive material. As a method for producing tricalcium phosphate, in general, a calcium source is mixed with a phosphoric acid source at a molar ratio of 3:2, and the mixture is then heated at 1200° C. or higher, so as to obtain an $\alpha$-type tricalcium phosphate. On the other hand, the aforementioned mixture is heated at 1000° C. or lower, so as to obtain $\beta$-type tricalcium phosphate. A specific example of the tricalcium phosphate that can be used herein is the tricalcium phosphate described in the Japanese Standards of Food Additives, which contains 98.0% to 103.0% of tricalcium phosphate $[Ca_3(PO_4)_2]$ when it is dried. This tricalcium phosphate described in the Japanese Standards of Food Additives is used as an anticaking agent for instant coffee, powdery milk products, condiments, powdered preparations, and the like, or as a calcium source for various types of food products.

The calcium carbonate may be derived from the natural products such as coral, or may also be derived from synthetic products such as calcium oxide, calcium chloride, calcium peroxide, calcium acetate, etc. There can be used the precipitated calcium carbonate described in the Japanese Pharmacopoeia, such as calcium carbonate containing 98.5% or more of calcium carbonate $[CaCO_3]$ when it is dried, or the calcium carbonate described in the Japanese Standards of Food Additives, such as calcium carbonate which contains 98.0% to 102.0% of calcium carbonate $[CaCO_3]$ when it is dried. These calcium carbonates are used as agents for improving antacid action in gastroduodenal ulcer or gastritis, calcium fortifiers for various types of food products, and the like.

The size of the calcium compound microparticle used in the present invention is preferably smaller than the particle size of a poorly-soluble substance. The smaller the particle size of the calcium compound microparticle, the larger the specific surface area that can be obtained, and as a result, the rate of coating the poorly-soluble substance can be enhanced. Thus, the size of the calcium compound microparticle is preferably as small as possible. Specifically, the present calcium compound microparticles are, for example, particles having a mean particle size of preferably 100 µm or less, more preferably 50 µm or less, further preferably 10 µm or less, and particularly preferably 1 µm or less. The lower limit of the particle size is not particularly limited. It is generally approximately 0.05 µm for production reasons. The mean particle size is measured using a Laser Diffraction/Scattering Particle Size Distribution Analyzer. Moreover, the specific surface area of the calcium compound microparticles is preferably 20 $m^2/g$ or more, and more preferably 30 $m^2/g$ or more. The upper limit thereof is not particularly limited, and it is, for example, approximately 200 $m^2/g$ or more. It is to be noted that, when the calcium compound microparticles are coated with a dispersing agent, the aforementioned size means the size or specific surface area of the particles, which have been coated with the dispersing agent. Furthermore, the form of the calcium compound microparticle may be any one of a spherical form, a platy form, an acicular form, and other forms.

In a case in which the after-mentioned method of applying mechanical energy to the calcium compound microparticles, so as to allow them to penetrate into a poorly-soluble substance particle, is used as a method of coating the poorly-soluble substance particle with the calcium compound microparticles, since the calcium compound microparticles are destructed by physical collision, the size of the calcium compound to be used may be greater than that of the poorly-soluble substance particle. If taking into consideration a collision rate for destruction and a collision rate for penetration, the same mean particle size as described above is preferable. Moreover, the size of the calcium compound microparticle to be penetrated into the poorly-soluble substance particle serving as a core is more preferably ⅕ or less, and further preferably 1/10 or less, of the size of the poorly-soluble substance particle because the state of the penetrated calcium compound microparticle can be more stably retained, when the microparticle has the aforementioned size.

The method of finely grinding the calcium compound is not particularly limited. A dry method, a wet method or the like can be applied, and a general dry mill or wet mill, etc. can be used, for example. For instance, a bead mill, a sand mill, a high-speed impact mill, a high-pressure wet atomizing unit, and the like can be used. Specific examples of the bead mill and sand mill include: Visco Mill manufactured by Aimex Co., Ltd.; Grain Mill manufactured by Asada Iron Works Co., Ltd.; Dyno-Mill manufactured by Sinmaru Enterprises Corp.; Anealler Mill manufactured by Mitsui Kozan K. K.; Sand Mill manufactured by Inoue Manufacturing Co., Ltd.; and Sand Mill manufactured by Kotobuki Engineering & Manufacturing Co., Ltd. An example of the high-speed impact mill is Ultra-High-Pressure Homogenizer manufactured by MIZUHO Industrial CO., LTD. Examples of the high-pressure wet atomizing unit include: Nanomizer manufactured by Yoshida Kikai Co., Ltd.; Atomization Apparatus manufactured by Sugino Machine Ltd.; and Atomization Apparatus manufactured by Microfluidics.

In the present invention, the calcium compound microparticles are preferably coated with a dispersing agent because the solubility of the poorly-soluble substance is thereby improved more effectively. Such coating with a dispersing agent can be carried out by adding the dispersing agent when the calcium compound is ground. Examples of such a dispersing agent include citric acid, citrate, and chondroitin sulfate. The amounts of the calcium compound microparticles coated with the dispersing agent are preferably 5% or more, more preferably 60% or more, further preferably 90% or more, and particularly preferably 100%.

As methods of coating the poorly-soluble substance with these calcium compound microparticles, conventionally known methods such as a wet granulation method, a dry granulation method, a spray granulation method, a fluidized-bed granulation method, a dipping method and a spray coating method can be used. A preferred coating method is a method comprising applying mechanical energy to the calcium compound microparticles by a mechanical fusion method or a hybridization method, so as to allow the calcium compound microparticles to penetrate into the poorly-soluble substance particle by physical compression, shearing force or impact force. Specific examples of such a coating method include: Mechanofusion System (Hosokawa Micron Group), Hybridization System (Nara Machinery Co., Ltd.), and Theta Composer (Tokuju Corp.). It is to be noted that, with regard to penetration of the calcium compound microparticles into the poorly-soluble substance particle, the calcium compound microparticle does not necessarily reach the center of the poorly-soluble substance particle, but it is sufficient if a part of the calcium compound microparticle penetrates into the poorly-soluble substance particle.

Moreover, the poorly-soluble substance may be coated with a single layer. Furthermore, even if the poorly-soluble substance is slightly coated, it exhibits the effect of improving the solubility of the substance. However, the surface of the particle of the poorly-soluble substance is coated at a percentage of preferably at least 5%, more preferably 60% or more, further preferably 90% or more, and particularly preferably 100%. Coating with a single layer provides sufficient effects, although the poorly-soluble substance may also be coated with two or more layers.

The type of the poorly-soluble substance used in the present invention is not particularly limited, as long as it is a substance having a property that it is hardly dissolved in water. It is a substance having a solubility (25° C.) of, for example, 10000 ppm or less, 5000 ppm or less, 3000 ppm or less, and 1000 ppm or less. Examples of such a poorly-soluble substance include: a substance acting as an active ingredient for pharmaceutical products, veterinary pharmaceutical products, quasi-drugs, cosmetic products and agricultural chemicals; and a food additive. Synthetic or natural polymeric substances, which are generally referred to as resins or rubbers, are not included in the present poorly-soluble substance. The size of the poorly-soluble substance is not particularly limited. Its mean particle size is preferably 0.5 to 2000 μm, more preferably 1 to 200 μm, and further preferably 5 to 50 μm. The mean particle size means a value measured using a Laser Diffraction/Scattering Particle Size Distribution Analyzer.

The poorly-soluble drug used in the present invention is a drug that is "sparingly soluble," "slightly soluble," "very slightly soluble," and "practically insoluble," which are defined in the Japanese Pharmacopoeia. The present poorly-soluble drug may have any dosage form of an oral preparation for internal application, an injection, a preparation for local administration, etc. Examples of such a poorly-soluble drug include an antitumor agent, an antibiotic, an antipyretic analgesic, an antihyperlipidemic agent, an antibacterial agent, a sedative hypnotic, a tranquilizer, an antiepileptic agent, an antidepressant, a gastrointestinal agent, an allergic disease therapeutic agent, an antihypertensive agent, a drug for arteriosclerosis, a blood circulation promoting agent, an antidiabetic agent, a hormonal agent, a fat-soluble vitamin, an antiandrogen agent, a cardiotonic drug, a drug for arrhythmia, a drug for diuresis, a local anesthetic, an anthelminthic, an antiarrhythmic agent, an anticoagulant, an antihistamic agent, an antimuscarinic agent, an antimycobacterial agent, an immunosuppressive agent, an antithyroid agent, an antiviral agent, an anxiolytic agent, an astringent, a β-adrenoreceptor blocker, an agent exerting inotropic action on cardiac muscle, a contrast medium, corticosteroid, a cough suppressing agent, a diagnostic agent, a diagnostic imaging agent, a diuretic, a dopamine agonist, a hemostatic agent, a lipid adjuster, a muscle relaxer, a parasympathetic drug, thyrocalcitonin and biphosphonate, prostaglandin, a radiopharmaceutical agent, sex hormone, a stimulant, an appetite suppressing agent, a sympathetic agent, a thyroid drug, a vasodilator, and xanthene.

Specific examples of the antitumor agent include HER2 inhibitors (heterocyclic compounds described in WO01/77107 and the like), melphalan, taxol, dacarbazine, doxorubicin hydrochloride, Neomycin hydrochloride, carmofur, methotrexate, enocitabine, etoposide, 5-fluorouracil, mitoxantrone, meson, dimesna, aminoglutethimide, tamoxifen, acrolein, cisplatin, carboplatin, cyclophosphamide, lomustine, carmustine, busulphan, para-aminosalicylic acid, mercaptopurine, tegafur, azathioprine, vinblastine sulfate, mitomycin C, ciclosporin, L-asparaginase, and ubenimex.

Examples of the antibiotic include amikacin, dibekacin, gentamycin, bacitracin, cephalexin, tetracycline, streptomycin, nystatin, erythromycin, fradiomycin sulfate, chloramphenicol, cefmetazole, and tolnaftate.

Examples of the antipyretic analgesic include aspirin, aspirin aluminum, aminopyrine, phenacetin, mefenamic acid, flufenamic acid, flufenamic acid aluminum, tolfenamic acid, acemetacin, indomethacin, alclofenac, diclofenac, ibuprofen, ibuprofenpiconol, oxyphenbutazone, phenylbutazone, ketophenylbutazone, clofezone, tiaramide hydrochloride, ketoprofen, diclofenac sodium, sulindac, naproxen, fenbufen, flurbiprofen, fenprofen, bufexamac, mepirizole, perisoxal citrate, glafenine, bucolome, pentazocine, metiazinic acid, protizinic acid, pranoprofen, fenoprofen calcium, piroxicam, feprazone, fentiazac, bendazac, dimethylisopropylazulene, glycyrrhetic acid, bufexamac, salicylic acid, acetaminophen, methyl salicylate, glycol salicylate, benzydamine, tialamide, tinoridine, ethenzamide, tenoxicam, chlortenoxicam, clidanac, naproxen, glycyrrhizin, glycyrrhetic acid, azulene, camphor, thymol, 1-menthol, sasapyrine, alclofenac, diclofenac, suprofen, loxoprofen, diflusinal, tiaprofenic acid, oxaprozin, and felbinac.

Examples of the antihyperlipidemic agent include clinofibrate, clofibrate, fenofibrate, bezafibrate, cholestyramine, soysterol, tocopherol nicotinate, nicomol, niceritrol, probucol, simvastatin, colestimide, and elastase.

Examples of the antibacterial agent include ofloxacin, ciprofloxacin hydrochloride, tosufloxacin tosilate, norfloxacin, lomefloxacin hydrochloride, pazufloxacin, rokitamycin, cefpodoxime proxetil, roxithromycin, midecamycin acetate, cefatrizine, josamycin propionate, and fosfomycin or a salt thereof.

Examples of the sedative hypnotic include barbital, amobarbital, amobarbital sodium, phenobarbital, phenobarbital sodium, secobarbital sodium, pentobarbital calcium, hexobarbital, triclofos, bromovalerylurea, glutethimide, methaqualone, perlapine, nitrazepam, flurazepam hydrochloride, flunitrazepam, and estazolam.

Examples of the tranquilizer include diazepam, lorazepam, and oxazolam.

Examples of the antiepileptic agent include phenytoin, phenobarbital, carbamazepine, primidone, phenacemide, ethylphenacemide, ethotoin, phensuximide, nitrazepam, and clonazepam.

Examples of the antidepressant include imipramine, noxiptiline, and phenelzine.

Examples of the gastrointestinal agent include aldioxa, irsogladine maleate, metoclopramide, cimetidine, famotidine, omeprazole, lansoprazole, enprostil, gefarnate, teprenone, sulpiride, trepibutone, oxethazain, and sucralfate.

Examples of the allergic disease therapeutic agent include clemastine fumarate, cyproheptadine hydrochloride, fexofenadine hydrochloride, ebastine, mequitazine, diphenhydramine, methdilazine, clemizole, and methoxyphenamine.

Examples of the antihypertensive agent include alacepril, nicardipine hydrochloride, delapril hydrochloride, captopril, cilnidipine, felodipine, barnidipine hydrochloride, efonidipine hydrochloride, amlodipine besylate, benidipine hydrochloride, nisoldipine, manidipine hydrochloride, nitrendipine, nilvadipine, trandolapril, valsartan, candesartan cilexetil, urapidil, carvedilol, prazosin hydrochloride, bunazosin hydrochloride, doxazosin mesilate, reserpine, methyldopa, guanabenz acetate, deserpidine, meptame, and meptamate.

Examples of the drug for arteriosclerosis include clofibrate, simfibrate, elastase, soysterol, and nicomol.

Examples of the blood circulation promoting agent include tocopherol acetate, benzyl nicotinate, tolazoline, verapamil, caffeine, cyclandelate, acetylcholine, and tocopherol nicotinate.

Examples of the antidiabetic agent include tolbutamide, glibenclamide, gliclazide, troglitazone, epalrestat, buformin, and metformin.

Examples of the hormonal agent include dexamethasone, dexamethasone acetate, betamethasone, betamethasone valerate, betamethasone dipropionate, beclometasone dipropionate, prednisolone, prednisolone valerate, prednisolone acetate, methylprednisolone, methylprednisolone acetate, hydrocortisone, hydrocortisone acetate, hydrocortisone acetate propionate, amcinonide, triamcinolone, triamcinolone acetonide, fluocinolone acetonide, hexestrol, methimazole, estriol, estriol tripropionate, clobetasone acetate, clobetasol propionate, fluocinonide, testosterone propionate, testosterone enanthate, fluoxymesterone, drostanolone propionate, estradiol benzoate, estradiol propionate, estradiol valerate, ethinylestradiol, mestranol, estriol benzoate diacetate, fluorometholone, fludroxycortide, diflucortolone valerate, halcinonide, progesterone, hydroxyprogesterone caproate, pregnanediol, medroxyprogesterone acetate, dimethisterone, norethisterone, allylestrenol, gestonorone caproate, and oxendolone.

Examples of the antiandrogen agent include oxendolone, allylestrenol, chlormadinone acetate, gestonorone caproate, osaterone acetate, flutamide, and bicalutamide.

Examples of the cardiotonic drug include digoxin, digotoxin, and ubidecarenone.

Examples of the drug for arrhythmia include pindolol, nadolol, bopindolol malonate, arotinolol hydrochloride, atenolol, lidocaine, propafenone hydrochloride, amiodarone hydrochloride, disopyramide, and carteolol hydrochloride.

Examples of the drug for diuresis include polythiazid, spironolactone, chlortalidone, triamteren, hydrochlorothiazide, and furosemide.

Examples of the local anesthetic include dibucaine hydrochloride, ethyl aminobenzoate, procaine hydrochloride, lidocaine, tetracaine hydrochloride, lidocaine hydrochloride, T-Cain, benzocaine, benzyl alcohol, pramoxine hydrochloride, quatacaine hydrochloride, butanicaine hydrochloride, piperocaine hydrochloride, and chlorobutanol.

Examples of the substance used in cosmetic products or quasi-drugs include methyl cinnamate, ethyl cinnamate, dl-α-tocopherol acetate, α-tocopherol (vitamin E), trichlorocarbanilide, eugenol, isoeugenol, ethyl methyl phenylglycidate, geranyl acetate, piperonal, hexyl laurate, ionone, cinnamyl acetate, decyl oleate, terpinyl acetate, triazine, anilide, benzophenone, triazole, cinnamide, sulfonated benzoimidazole, carotene, piroctone olamine, minoxidil, phytosteside, tocopherol nicotinate, ethinyl estradiol, polyporusterone, ecdysteroids, and various types of perfumes.

Examples of the substance used in food and drink products include L-ascorbyl stearate, benzoic acid, ionone, isoeugenol, ergocalciferol (vitamin $D_2$), eugenol, butyl parahydroxybenzoate, isopropyl parahydroxybenzoate, β-carotene, citronellyl formate, cholecalciferol (vitamin $D_3$), cinnamyl acetate, phenethyl acetate, ethyl cinnamate, dibutylhydroxytoluene, allyl hexanoate, propyl gallate, methyl β-methyl ketone, folic acid, riboflavine tetrabutyrate, lecithin, and dl-α-tocopherol.

Examples of the agricultural chemical include poorly-soluble agricultural chemical active ingredients having insecticidal action, germicidal action, herbicidal action, plant growth regulatory and other actions, such as a substance having a solubility in water (25° C.) of 1000 ppm or less.

Specifically, examples of the poorly-soluble insecticidal substance include abamectin, acrinathrin, amitraz, azadirachtin, azamethiphos, azinphos-methyl, azocyclotin, ethofenprox, ethylthiometon, chlorpyrifos methyl, bensultap, bifenthrin, bromopropylate, buprofezin, carbaryl, chlorfenapyr, chlorfenson, chlorfluazuron, clofentezine, coumaphos, diazinon, cycroprothrin, cyfluthrin, β-cyfluthrin, cypermethrin, α-cypermethrin, θ-cypermethrin, deltamethrin, diafenthiuron, dicofol, diflubenzuron, carbosulfan, endosulfan, esfenvalerate, etoxazole, fenazaquin, fenbutatin oxide, fenoxycarb, fenpyroximate, fipronil, fluazuron, flucycloxuron, flufenoxuron, flubendiamide, fenthion, halofenozide, hexaflumuron, hexythiazox, hydramethylnon, metaflumizone, lufenuron, methiocarb, methoxychlor, milbemycin, novaluron, pentachlorophenol, pyridaben, rotenone, sulfluramid, tebufenozide, tebufenpyrad, tebupirimfos, teflubenzuron, tetrachlorvinphos, tetradifon, thiodicarb, benfuracarb, tralomethrin, tolfenpyrad, triflumuron, trimethacarb, furathiocarb, and bendiocarb.

Examples of the poorly-soluble germicidal substance include azoxystrobin, isoprothiolane, benalaxyl, benomyl, bitertanol, bromuconazole, captafol, captan, carpropamide, carbendazim, chinomethionate, chlorothalonil, chlozolinate, cyprodinil, dichlofluanid, diclofen, diclomezine, dicloran, diclocymet, diethofencarb, dimethomorph, diniconazole, dithianon, tiadinil, epoxiconazole, famoxadone, fenarimol, fenbuconazole, fenfuram, fenpiclonil, fentin, fluazinam, fludioxonil, fluoroimide, fluquinconazole, flusulfamide, flutolanil, folpet, hexachlorobenzene, hexaconazole, imibenconazole, ipconazole, iprodione, kresoxim-methyl, manzeb, maneb, mepanipyrim, mepronil, metconazole, metiram, nickel bis(dimethyldithiocarbamate), nuarimol, oxine copper, oxolinic acid, pencycuron, phthalide, procymidone, propineb, quintozene, sulfur, tebuconazole, tecloftalam, tecnazene, thifluzamide, thiophanete-methyl, thiram, tolclofos-methyl, tolylfluanide, triadimefon, triadimenol, triazoxide, triforine, triticonazole, vinclozolin, zineb, and ziram.

Examples of the poorly-soluble herbicidal substance include azafenidin, thenylchlor, bifenox, sulfentrazone, pyraflufen-ethyl, flumiclorac-pentyl, flumioxazin, aclonifen, atrazine, indanofan, bensulfuron methyl, benzofenap, bromobutide, bromofenoxim, chlomethoxyfen, chlorbromuron, chlorimuron ethyl, chlornitrofen, chlortoluron, chlorthal-dimethyl, clomeprop, dymron, desmedipham, dichlobenil, diflufenican, dimefuron, dinitramine, diuron, ethametsulfuron methyl, traiziflam, fenoxaprop-ethyl, flamprop-methyl, flazasulfuron, flumetsulam, fluthiacet-methyl, flupoxam, fluridone, flurtamone, oxaziclomefone, isoproturon, isoxaben, isoxapyrifop, lactofen, lenacil, linuron, mefenacet, methabenzthiazuron, metobenzuron, naproanilide, neburon, norflurazon, oryzalin, oxadiazon, oxyfluorfen, phenmedipham, prodiamine, prometryn, propazine, propyzamide, pyrazolynate, pyrazosulfuron-ethyl, pyributicarb, quinclorac, quizalofop ethyl, rimsulfuron, siduron, simazine, terbuthylazine, terbutryn, thiazopyr, tralkoxydim, and trietazine.

Examples of the poorly-soluble plant growth regulatory substance include 6-benzylaminopurine, cyclanilide, flumetralin, forchlorfenuron, inabenfide, 2-(1-naphtyl)acetamide, paclobutrazol, n-phenylphthalamidic acid, thidiazuron, and uniconazole.

The substance with improved aqueous solubility obtained by the production method of the present invention can be used by mixing it into pharmaceutical products, veterinary pharmaceutical products, quasi-drugs, cosmetic products, agricultural chemicals, food products, and the like. The forms of the pharmaceutical products, veterinary pharmaceutical products, quasi-drugs, cosmetic products, agricultural chemicals, and food products are not particularly limited. The forms may be either solid compositions such as a tablet, granule or powder, or aqueous liquid compositions containing water. As a result of the improvement of solubility according to the present invention, a substance, which has not sufficiently exhibited effects due to its poor solubility, can exhibit the effects.

EXAMPLES

1. Preparation of Coating Agent

A. [Preparation of Hydroxyapatite]

A phosphoric acid aqueous solution in a 30 wt % concentration was added dropwise to a calcium hydroxide suspension under stirring, until the Ca/P ratio became 1.67. The thus generated gelatinous substance was left at a room temperature for 1 day, so as to age it. Thereafter, this gelatinous substance was filtrated with a glass filter, and the remaining substance was then dried in the air at 100° C. The resultant was ground with a mixer, so as to obtain hydroxyapatite.

B. [Preparation of Hydroxyapatite Microparticles by Dry Method]

The hydroxyapatite obtained in the above section [Preparation of hydroxyapatite] (hereinafter simply referred to as "hydroxyapatite") was finely ground using a jet mill (Co-Jet System α-mkII, manufactured by Seishin Enterprise Co., Ltd.), so as to obtain hydroxyapatite microparticles according to a dry method.

C. [Preparation of Microparticles by Wet Method]

Hydroxyapatite, tricalcium phosphate, and calcium carbonate were suspended in water to obtain a 20% suspension. This was then ground employing a Dyno-Mill (ECM-PILOT, manufactured by Willy A. Baechofen AG Machinenfabrik Basel) using 0.3-mm zirconia beads. The particle size distribution was measured every 30 minutes, and grinding was terminated at the time point in which almost no change was found in the particle size, so as to produce by a wet method, (1) hydroxyapatite microparticles, (2) tricalcium phosphate microparticles, and (3) calcium carbonate microparticles. It is to be noted that a food additive (Wako Pure Chemical Industries, Ltd.) was used as tricalcium phosphate, and that a guaranteed reagent (Wako Pure Chemical Industries, Ltd.) was used as calcium carbonate (the same applies below).

D. [Preparation of Microparticles with Surface Coated with Dispersing Agent (Sodium Citrate)]

Hydroxyapatite, tricalcium phosphate, and calcium carbonate were added to a 200 mM sodium citrate solution, so that they each become a 20% suspension. The obtained suspension was ground employing a Dyno-Mill using 0.3-mm zirconia beads. The particle size distribution was measured every 30 minutes, and grinding was terminated at the time point in which almost no change was found in the particle size. Thereafter, sodium citrate and the like contained in the solution were removed, and the residue was then dried, so as to obtain (1) hydroxyapatite microparticles, (2) tricalcium phosphate microparticles, and (3) calcium carbonate microparticles, each surface of which was coated with the dispersing agent (sodium citrate).

E. [Preparation of Moderately Ground Hydroxyapatite Microparticles with Surface Coated with Dispersing Agent (Sodium Citrate)]

Hydroxyapatite was added to a 200 mM sodium citrate solution to obtain a 20% suspension. The obtained suspension was ground for 30 minutes employing a Dyno-Mill using 1.0-mm zirconia beads. Thereafter, sodium citrate and the like contained in the solution were removed, and the residue was then dried, so as to obtain moderately ground hydroxyapatite microparticles, each surface of which was coated with the dispersing agent (sodium citrate).

F. [Preparation of Hydroxyapatite Particles with Surface Coated with Dispersing Agent (Sodium Citrate)]

Hydroxyapatite was added to a 200 mM sodium citrate solution to obtain a 20% suspension. The obtained suspension was moderately stirred for 60 minutes. Thereafter, sodium citrate and the like contained in the solution were removed, and the residue was then dried, so as to obtain hydroxyapatite particles, each surface of which was coated with the dispersing agent (sodium citrate).

G. [Preparation of Hydroxyapatite Microparticles with Surface Coated with Dispersing Agent (Pyrophosphoric Acid)]

Hydroxyapatite was added to a 200 mM sodium citrate solution to obtain a 20% suspension. The obtained suspension was ground for 60 minutes employing a Dyno-Mill using 0.3-mm zirconia beads. Thereafter, pyrophosphoric acid and the like contained in the solution were removed, and the residue was then dried, so as to obtain hydroxyapatite microparticles, each surface of which was coated with the dispersing agent (pyrophosphoric acid).

2. Measurement of Particle Sizes of Coating Agents

The particle sizes of various types of coating particles obtained in the above described preparation methods were measured using a Laser Diffraction/Scattering Particle Size Distribution Analyzer (manufactured by Horiba, Ltd.). The results are shown in Table 1.

TABLE 1

Particle diameters of coating agents

| Composition | Particle diameter (μm) |
|---|---|
| A. Hydroxyapatite particles | 9.499 |
| B. Hydroxyapatite microparticles prepared by dry method | 0.839 |
| C. (1) Hydroxyapatite microparticles prepared by wet method | 0.516 |
| C. (2) Tricalcium phosphate microparticles prepared by wet method | 11.565 |
| C. (3) Calcium carbonate microparticles prepared by wet method | 13.426 |
| D. (1) Hydroxyapatite microparticles with surface coated with disperser<br>Disperser: sodium citrate | 0.102 |
| D. (2) Tricalcium phosphate microparticles with surface coated with disperser<br>Disperser: sodium citrate | 1.631 |
| D. (3) Calcium carbonate microparticles with surface coated with disperser<br>Disperser: sodium citrate | 0.426 |
| E. Moderately ground hydroxyapatite particles with surface coated with disperser<br>Disperser: sodium citrate | 1.13 |
| F. Hydroxyapatite particles with surface coated with disperser<br>Disperser: sodium citrate | 3.62 |
| G. Hydroxyapatite microparticles with surface coated with disperser<br>Disperser: pyrophosphoric acid | 2.36 |

3. Measurement of Specific Surface Areas of Coating Agents

The specific surface areas of various types of coating particles obtained in the above described preparation methods were measured (Specific Surface Area Measurement Device SA3100, manufactured by COULTER). The measurement was carried out by a nitrogen gas adsorption method under degassing conditions at 150° C. for 20 minutes. The results are shown in Table 2.

TABLE 2

Specific surface areas of coating agents

| Composition | Specific surface area (m²/g) |
|---|---|
| A. Hydroxyapatite particles | 33.0 |
| B. Hydroxyapatite microparticles prepared by dry method | 34.0 |
| C. (1) Hydroxyapatite microparticles prepared by wet method | 62.8 |
| C. (2) Tricalcium phosphate microparticles prepared by wet method | 35.2 |
| C. (3) Calcium carbonate microparticles prepared by wet method | 20.4 |
| D. (1) Hydroxyapatite microparticles with surface coated with disperser<br>Disperser: sodium citrate | 122.9 |
| D. (2) Tricalcium phosphate microparticles with surface coated with disperser<br>Disperser: sodium citrate | 68.1 |
| D. (3) Calcium carbonate microparticles with surface coated with disperser<br>Disperser: sodium citrate | 33.4 |
| E. Moderately ground hydroxyapatite particles with surface coated with disperser<br>Disperser: sodium citrate | 31.8 |
| F. Hydroxyapatite particles with surface coated with disperser<br>Disperser: sodium citrate | 24.8 |
| G. Hydroxyapatite microparticles with surface coated with disperser<br>Disperser: pyrophosphoric acid | 80.7 |

4. Preparation of Hydroxyapatite for Use in Comparative Tests

[Hydroxyapatite Used as Mother Nucleus]

A phosphoric acid aqueous solution in a 30 wt % concentration was added dropwise to a calcium hydroxide suspension under stirring, until the Ca/P ratio became 1.67. The thus generated gelatinous substance was left at a room temperature for 1 day, so as to age it. Thereafter, this gelatinous substance was filtrated with a glass filter, and the remaining substance was then dried in the air at 100° C., so as to obtain hydroxyapatite used as a mother nucleus. The mean particle size was 20 to 30 μm.

[Porous Hydroxyapatite]

Hydroxyapatite, and the powder of Methyl Cellulose 4000 (Wako Pure Chemical Industries, Ltd.) that was in almost an equal amount of the hydroxyapatite, were placed in a beaker, and they were then fully blended. Then, ion exchange water was gradually added to the mixture, so as to make the hydroxyapatite and the methyl cellulose into balls. Thereafter, ion exchange water was added to the mixed powders that were in a state of balls, such that the balls could be fully immersed in the ion exchange water, and they were then treated with an ultrasonic cleaner for 5 hours. During the treatment, the methyl cellulose was gradually swollen, and the entire volume was thereby increased. Thus, ion exchange water was added. After completion of the ultrasonic treatment, the mixture was slowly dried with a constant-temperature dryer in which the temperature was kept at 70° C. Thereafter, the mixture was ground into an appropriate size, and was then sintered at 1200° C. for 5 hours, so as to obtain porous hydroxyapatite. This porous hydroxyapatite had a particle size of 9.242 μm and a specific surface area of 56.1 m²/g.

5. Measurement of Particle Sizes of Poorly-Soluble Substances

The particle sizes of poorly-soluble substances were measured using a Laser Diffraction/Scattering Particle Size Distribution Analyzer (manufactured by Horiba, Ltd.). The results are shown in Table 3.

TABLE 3

Particle diameters of poorly-soluble substances

| | Poorly-soluble substances | Particle diameter(μm) |
|---|---|---|
| 1 | Aspirin | 1987.653 |
| 2 | Bezafibrate | 114.319 |
| 3 | Chlormadinone acetate | 4.775 |
| 4 | Omeprazole | 9.896 |
| 5 | Probucol | 12.544 |
| 6 | Triamterene | 19.937 |
| 7 | Tolbutamide | 125.714 |

TABLE 3-continued

Particle diameters of poorly-soluble substances

| | Poorly-soluble substances | Particle diameter(μm) |
|---|---|---|
| 8 | Amoxicillin | 5.591 |
| 9 | Cisplatin | 45.732 |
| 10 | Trichlorocarbanilide | 8.410 |
| 11 | Glibenclamide | 27.129 |
| 12 | Atenolol | 30.746 |
| 13 | Trimethoprim | 154.208 |
| 14 | Primidone | 15.182 |

6. Preparation of Substances with Improved Aqueous Solubility 6-1. For use in Examples
[Coating of Poorly-Soluble Substances with Calcium Compound Microparticles According to Mechanofusion System]

Using Mechanofusion System AMS-MINI-GMP (Hosokawa Micron Group), a poorly-soluble substance was coated with calcium compound microparticles.

A poorly-soluble substance and calcium compound microparticles were placed in a Mechanofusion System Device, while changing the ratio between the poorly-soluble substance and the calcium compound microparticles. They were placed in the device to a total amount of 90 g/once, and thereafter, a coating treatment was carried out. During the coating treatment, the jacket portion of the device was cooled with alcohol, so that the temperature of the portion became 20° C. or lower. Moreover, in order to prevent the rotation load from exceeding 2.0 A, the coating treatment was carried out at a rotation number of 1250 to 4000 rpm for 15 to 60 minutes. In the case of products, which could be subjected to a coating treatment at a rotation number of 4000 rpm, the coating treatment was carried out for 15 minutes. On the other hand, in the case of products whose rotation load exceeded 2.0 A, and consequently, the rotation number became 4000 rpm or less, a coating treatment time was increased due to the rotation number. Thus, a coating treatment at the fewest rotation number (1250 rpm) was carried out for 60 minutes as the longest coating treatment time.

[Coating of Poorly-Soluble Substances with Calcium Compound Microparticles Using Hybridization System]

Using Hybridization System NHS-1 (Nara Machinery Co., Ltd.), a poorly-soluble substance was coated with calcium compound microparticles.

A mixture previously obtained by blending a poorly-soluble substance with calcium compound microparticles was placed in the Hybridization System, while changing the ratio between the poorly-soluble substance and the calcium compound microparticles. They were placed in the system to a total amount of 100 g/once, and thereafter, a coating treatment was carried out at 3000 rpm for 5 minutes.

[Coating of Poorly-Soluble Substances with Calcium Compound Microparticles Using Coating Pan]

Coating of a poorly-soluble substance with calcium compound microparticles was carried out using Coating Pan No. 16D (Kikusui Seisakusho Ltd.). As a binder, Ethyl Cellulose (approximately 49% ethoxy) 10 (Wako Pure Chemical Industries, Ltd.) was used.

Ethyl cellulose was dissolved in a concentration of 1% in acetone, and thereafter, calcium compound microparticles were suspended in the solution. While poorly-soluble substance particles were moderately stirred on a coating pan, the suspension of calcium compound microparticles was sprayed to the poorly-soluble substance particles. Drying and spraying were repeatedly carried out, and as a result, the poorly-soluble substance particles were coated with predetermined amounts of the calcium compound microparticles.

6-2. For Use in Comparative Tests
[Coating of Various Types of Mother Nucleus Particles with Poorly-Soluble Substances Using Hybridization System]

Using Hybridization System NHS-1 (Nara Machinery Co., Ltd.), various types of mother nucleus particles were coated with poorly-soluble substances.

A poorly-soluble substance had previously been mixed with the hydroxyapatite prepared in the above section [Hydroxyapatite used as mother nucleus] in equal weights. The thus obtained mixture was placed in a total amount of 100 g/once in the Hybridization System, and a coating treatment was then carried out at 3000 rpm for 5 minutes.

At the same time, crystalline cellulose was used instead of the hydroxyapatite prepared in the above section [Hydroxyapatite used as mother nucleus], and the same coating treatment as described above was then carried out.

[Impregnation of Porous Hydroxyapatite with Poorly-Soluble Substances]

The porous hydroxyapatite prepared in the above section [Porous hydroxyapatite] was added in an amount of 20 times the weight of poorly-soluble substances into a solution prepared by dissolving the poorly-soluble substances in a solvent, and the mixed solution was then left at an ordinary temperature under a negative pressure until the solvent completely disappeared, so that the porous hydroxyapatite particles were impregnated with the poorly-soluble substances.

Figure 2:
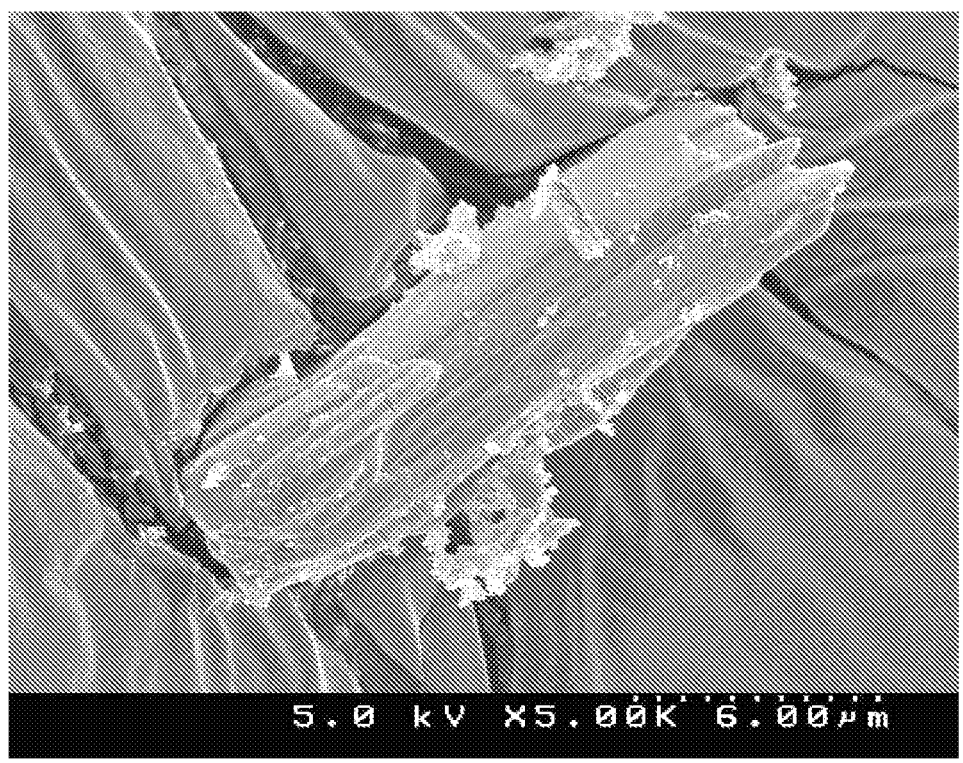
FIG. 2 shows an electron micrograph (10000-fold) of the aspirin of Example 1-2 that is 5% coated with hydroxyapatite.
Figure 3:
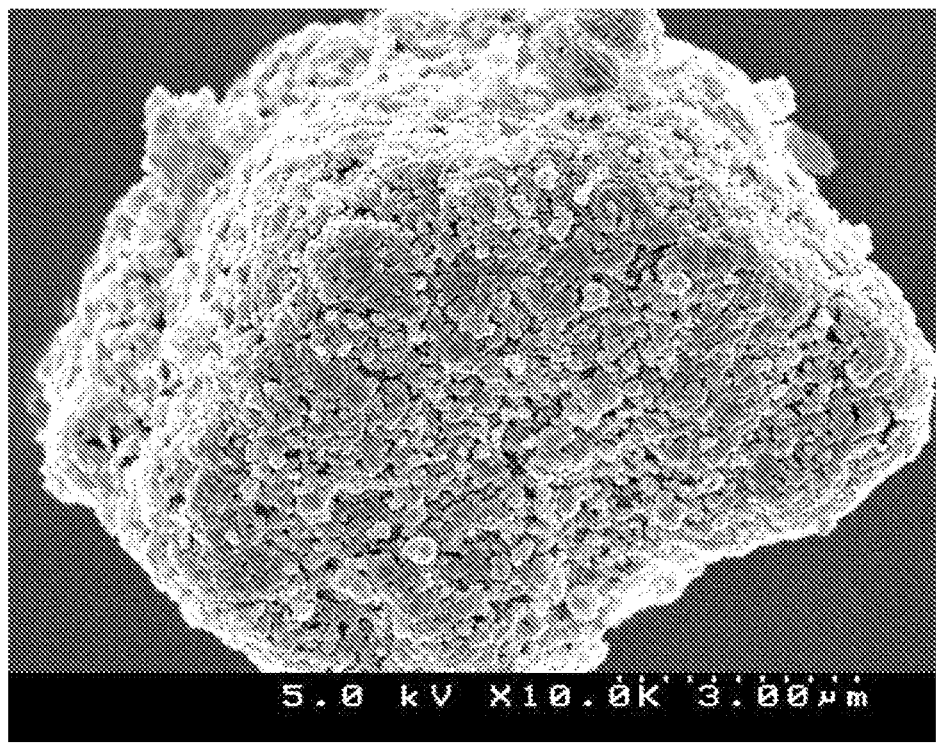
FIG. 3 shows an electron micrograph (10000-fold) of the aspirin of Example 1-3 that is 100% coated with tricalcium phosphate.
Figure 4:
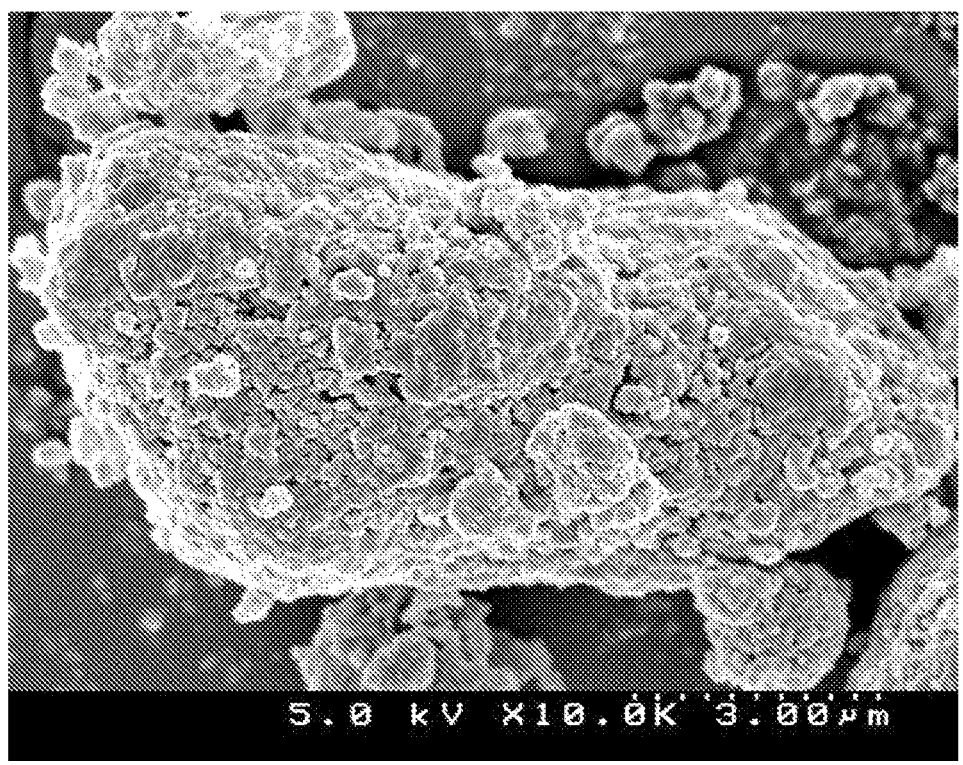
FIG. 4 shows an electron micrograph (10000-fold) of the aspirin of Example 1-4 that is 100% coated with calcium carbonate.
Figure 5:
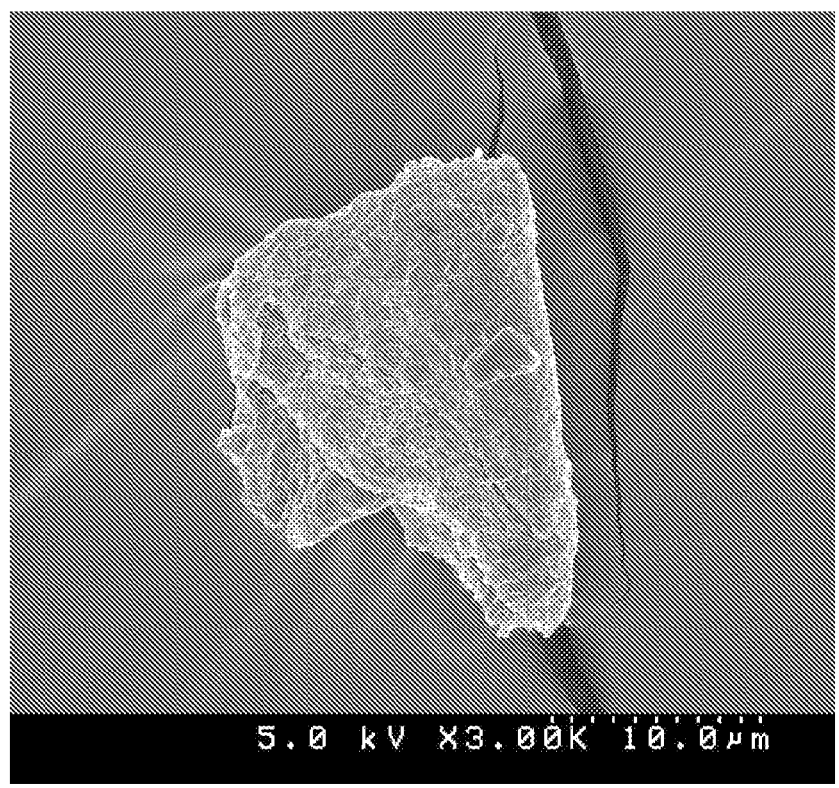
FIG. 5 shows an electron micrograph (3000-fold) of the aspirin of Comparative Example 1-3.
Figure 6:
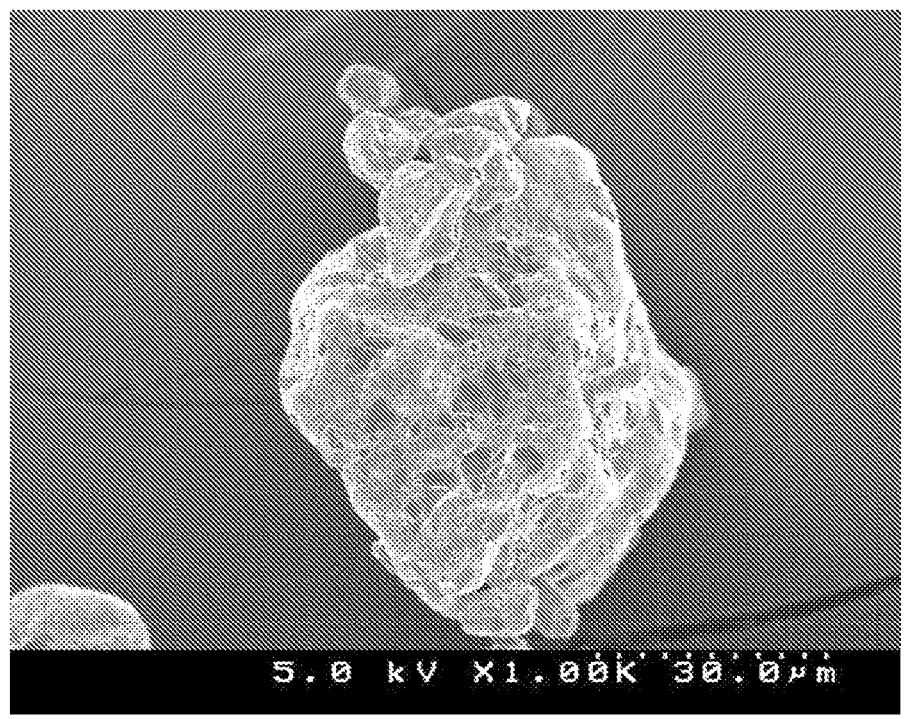
FIG. 6 shows an electron micrograph (1000-fold) of the bezafibrate of Example 2-2 that is 80% coated with hydroxyapatite.
Figure 7:
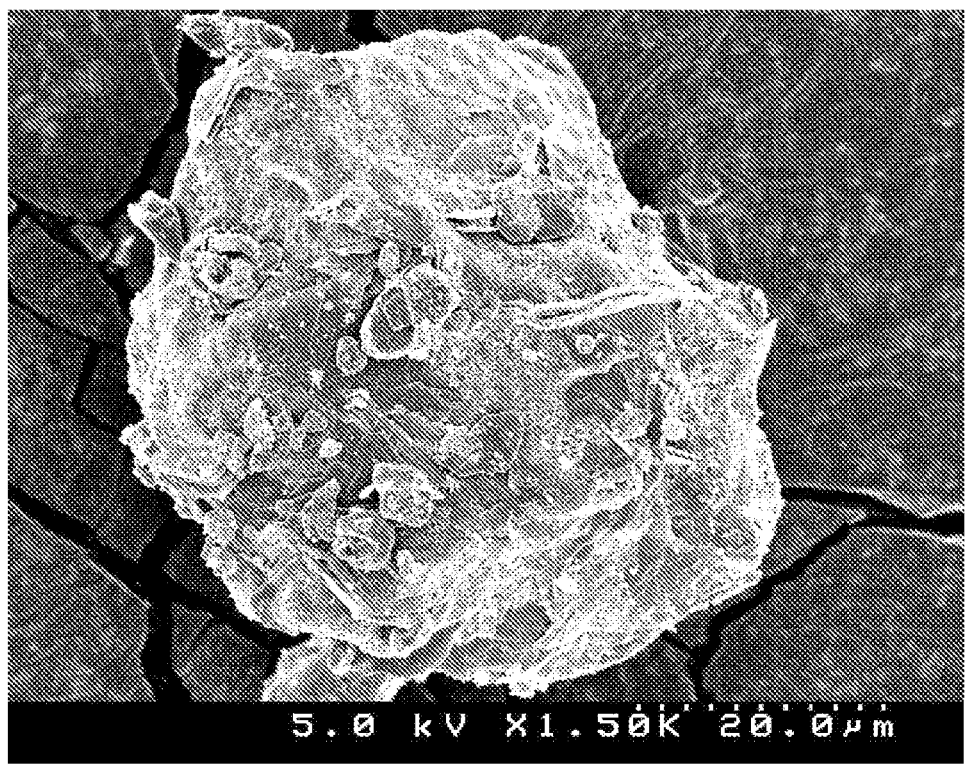
FIG. 7 shows an electron micrograph (1500-fold) of the bezafibrate of Example 2-3 that is 60% coated with hydroxyapatite.
Figure 8:
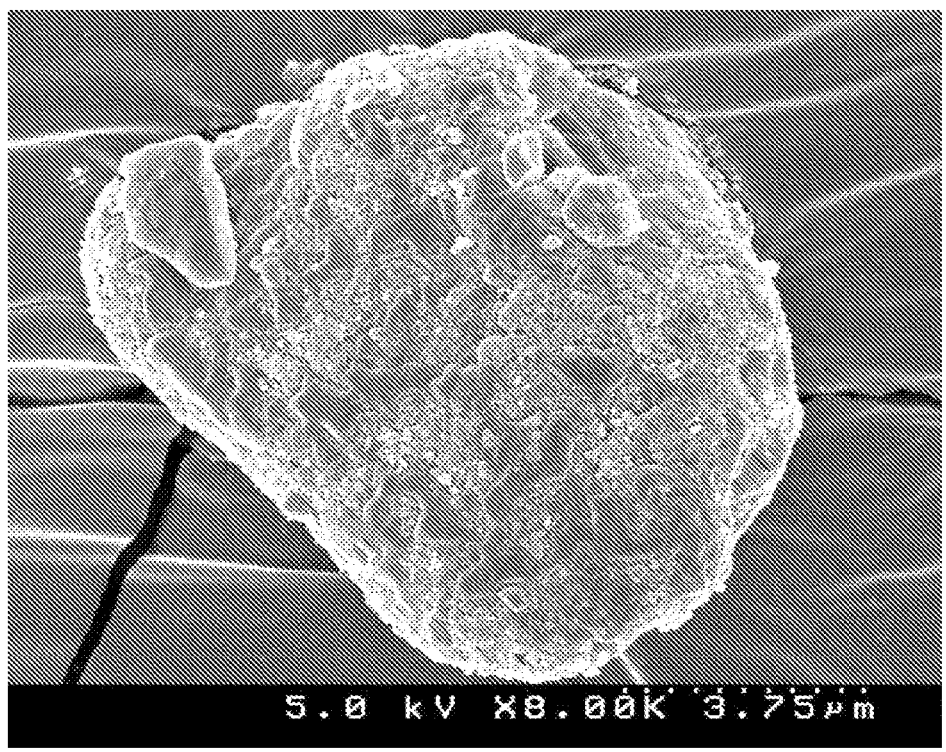
FIG. 8 shows an electron micrograph (8000-fold) of the bezafibrate that is 30% coated with hydroxyapatite.
Figure 9:
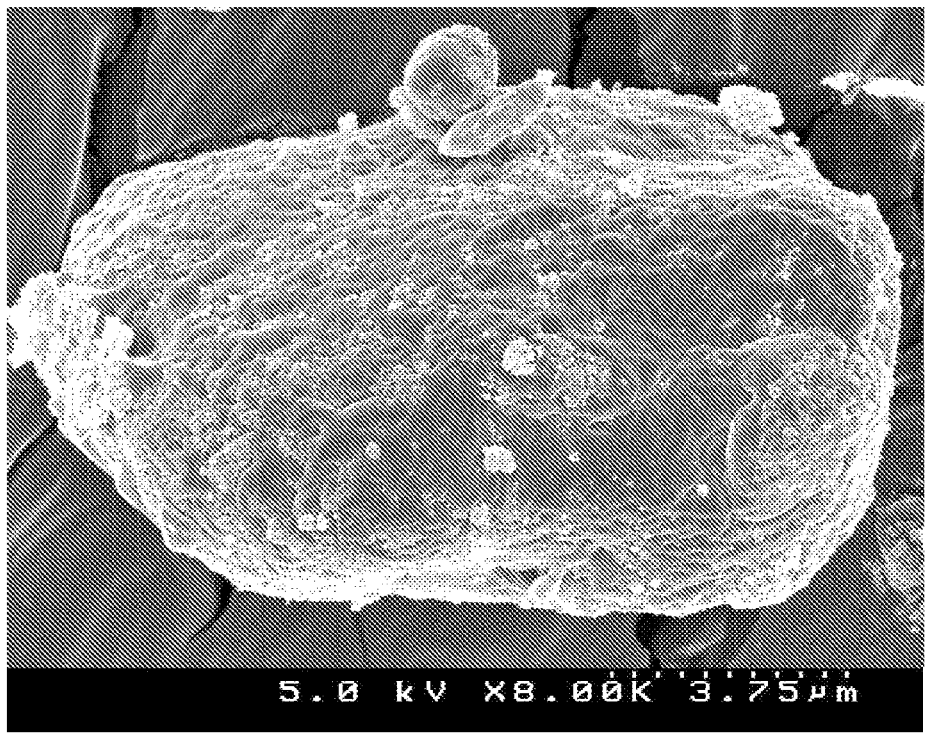
FIG. 9 shows an electron micrograph (8000-fold) of the bezafibrate of Example 2-4 that is 10% coated with hydroxyapatite.
Figure 10:
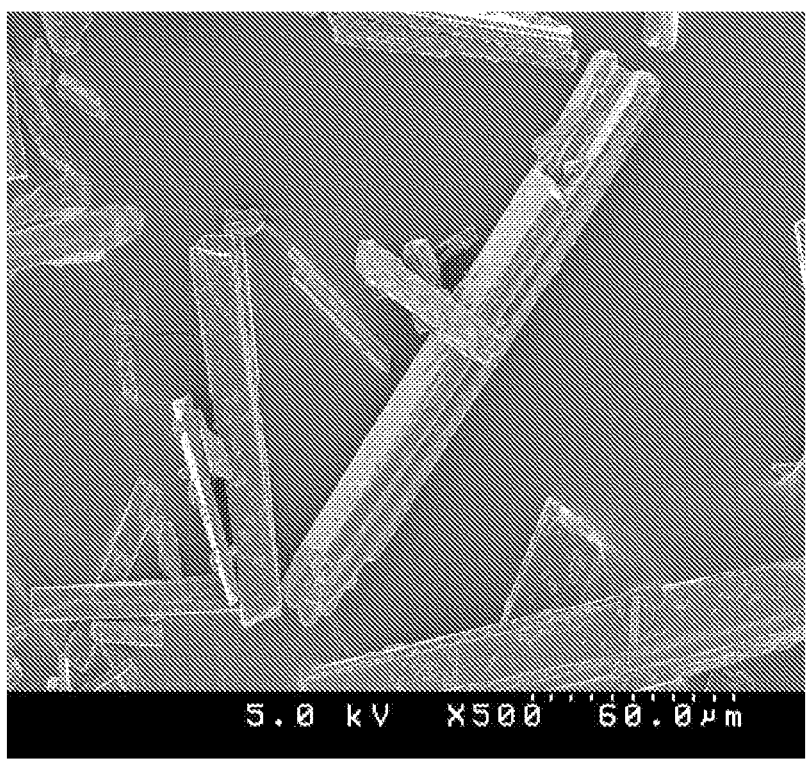
FIG. 10 shows an electron micrograph (500-fold) of the bezafibrate of Comparative Example 2-3.
Figure 11:
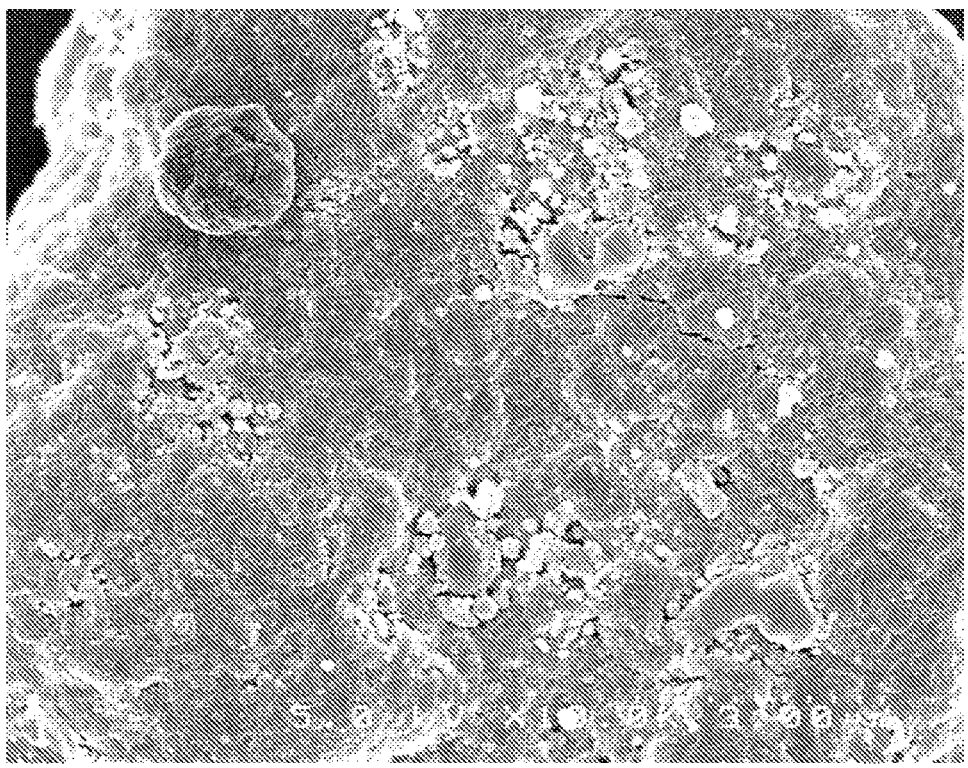
FIG. 11 shows an electron micrograph (10000-fold) of the chlormadinone acetate of Example 3-1 that is 100% coated with hydroxyapatite.
Figure 12:
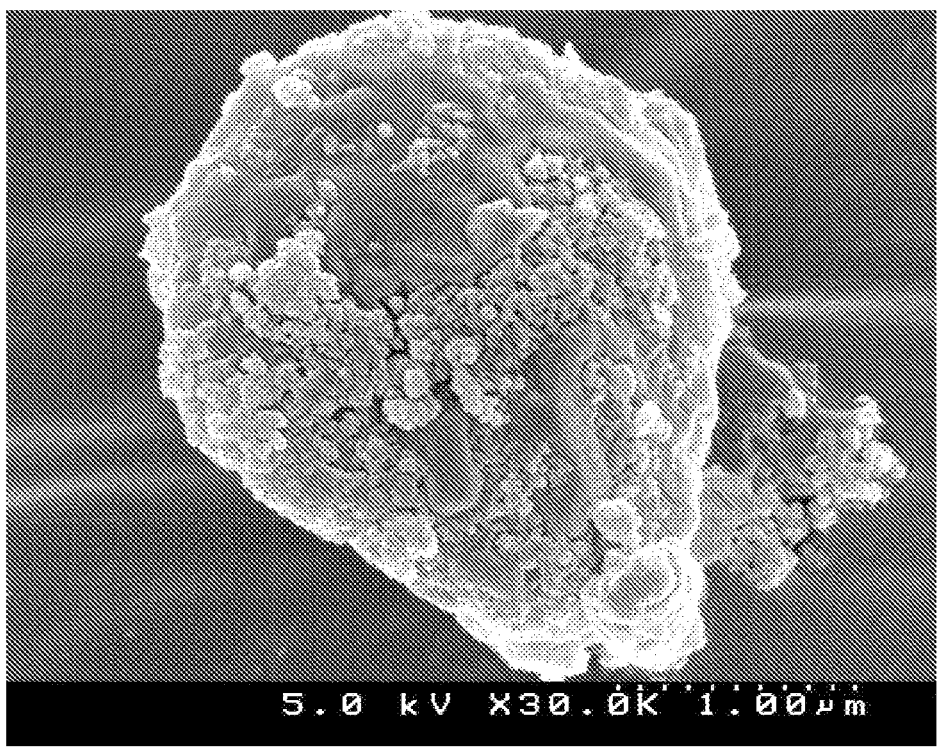
FIG. 12 shows an electron micrograph (30000-fold) of the chlormadinone acetate of Example 3-3 that is 30% coated with hydroxyapatite.
Figure 13:
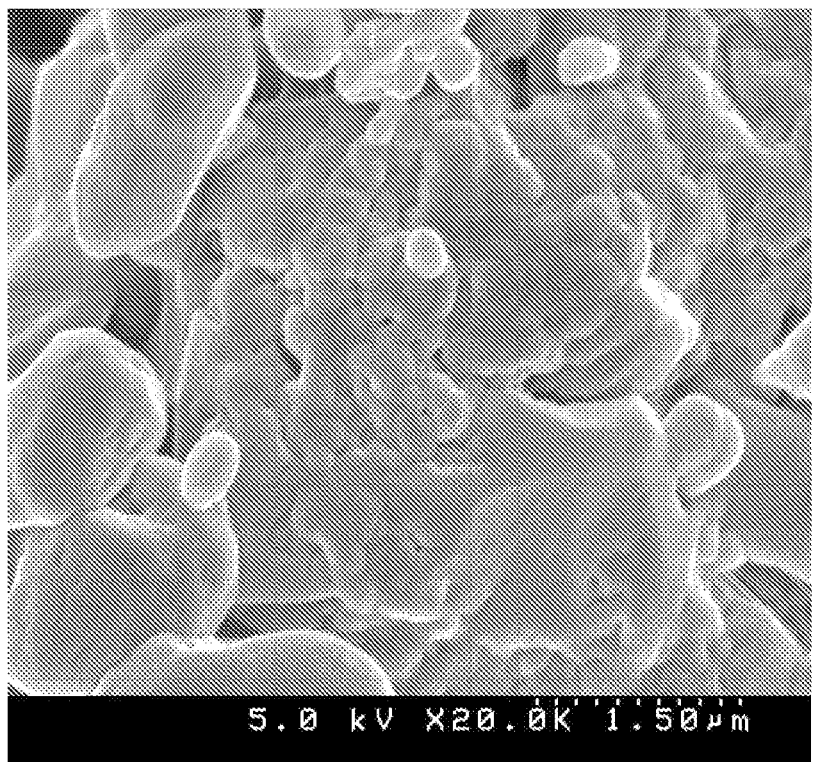
FIG. 13 shows an electron micrograph (20000-fold) of the chlormadinone acetate of Comparative Example 3-2.
Figure 14:
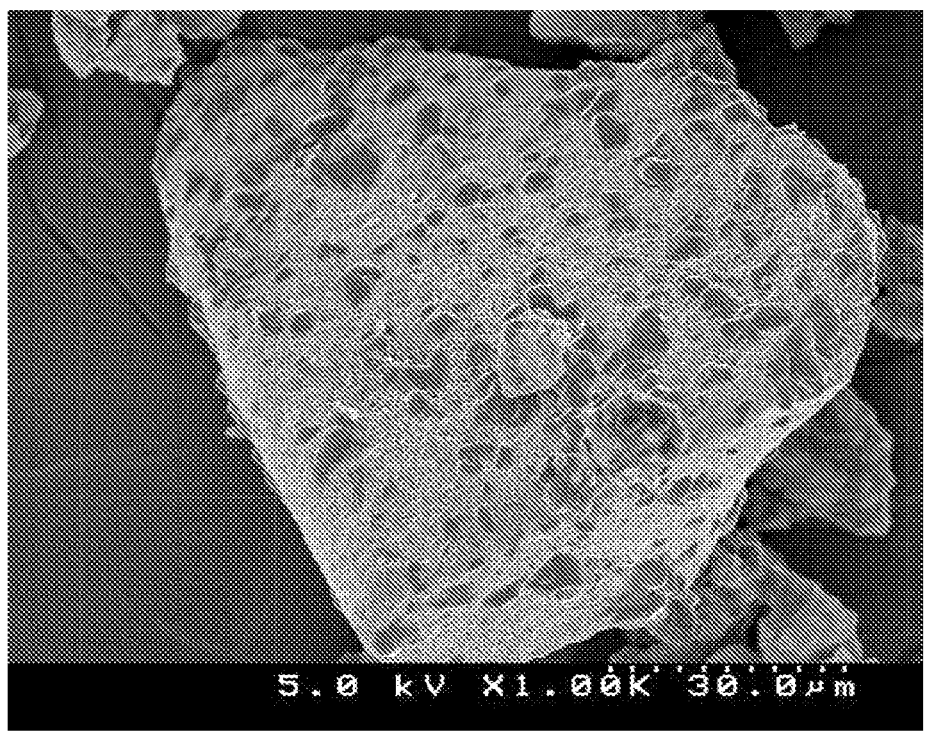
FIG. 14 shows an electron micrograph (1000-fold) of the probucol of Example 5-2 that is 70% coated with hydroxyapatite.
Figure 15:
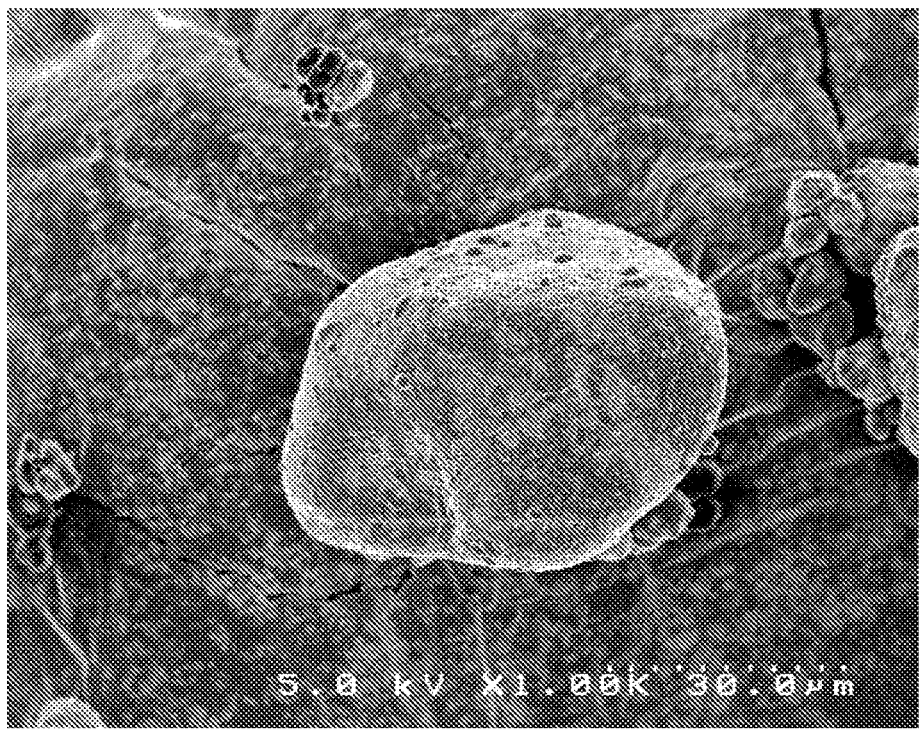
FIG. 15 shows an electron micrograph (1000-fold) of the probucol of Example 5-3 that is 50% coated with hydroxyapatite.
Figure 16:
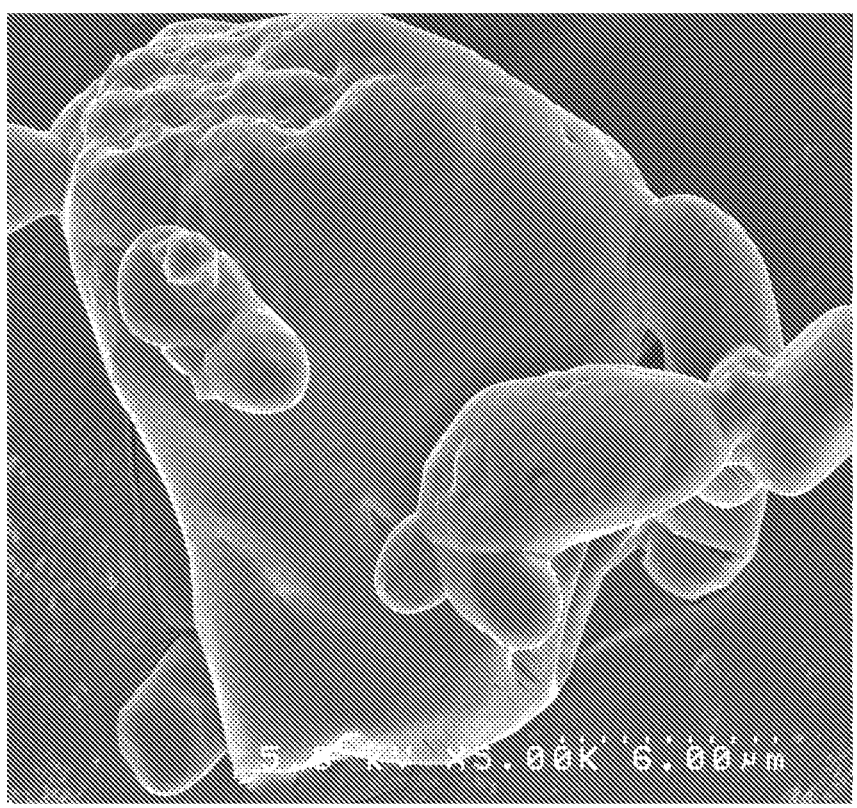
FIG. 16 shows an electron micrograph (5000-fold) of the probucol of Comparative Example 5-3.
Figure 17:
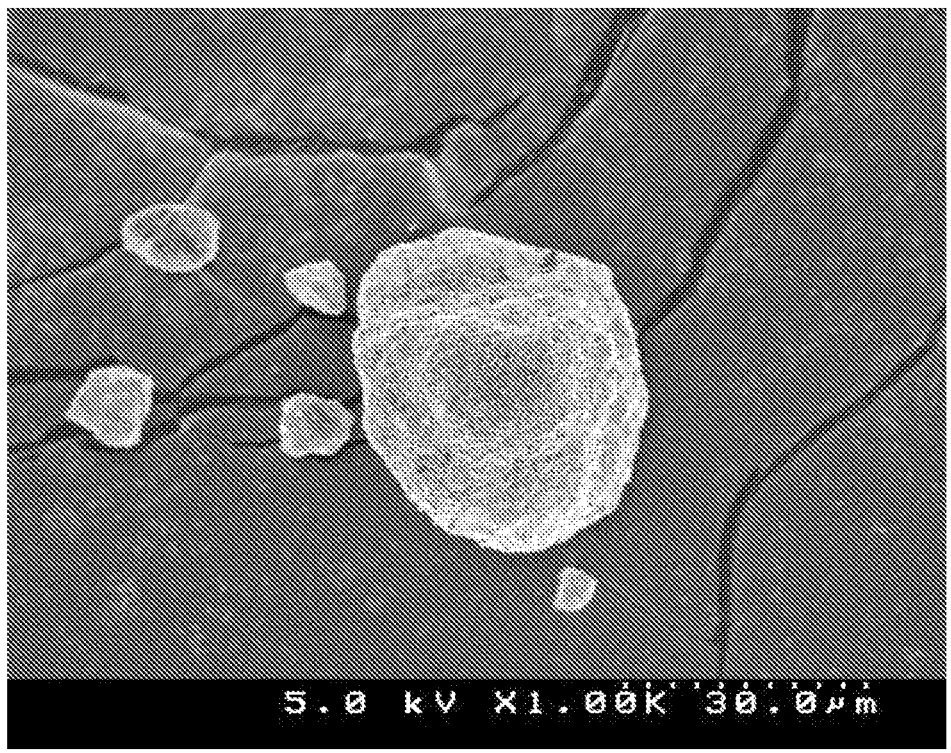
FIG. 17 shows an electron micrograph (1000-fold) of the tolbutamide of Example 7-1 that is 100% coated with hydroxyapatite.
Figure 18:
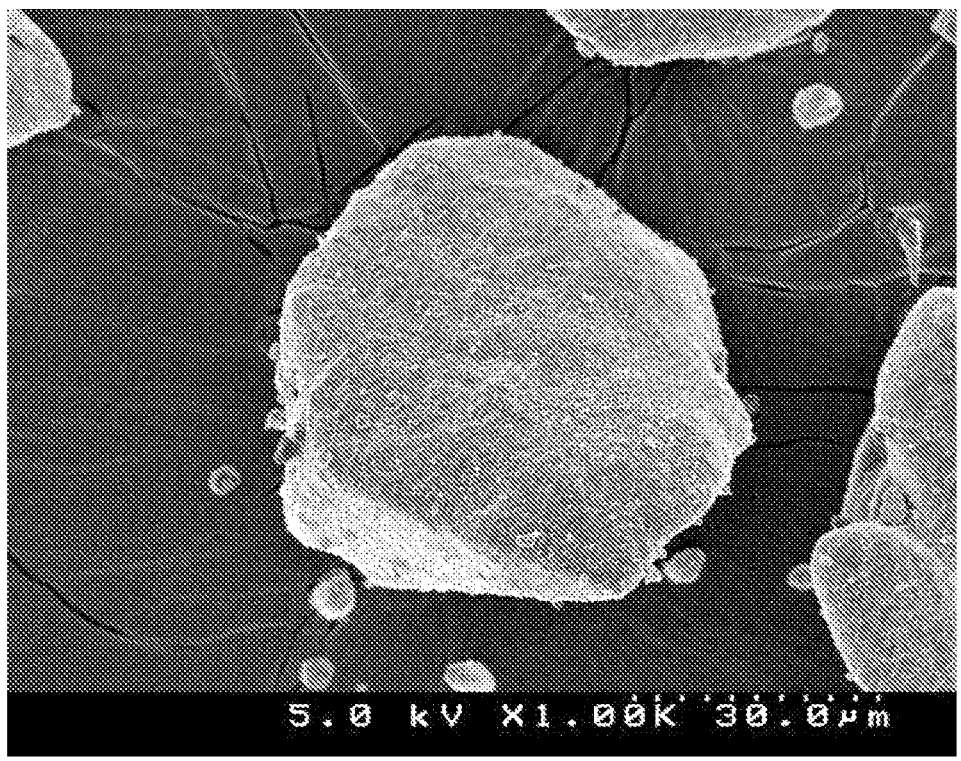
FIG. 18 shows an electron micrograph (1000-fold) of the tolbutamide that is 100% coated with tricalcium phosphate.
Figure 19:
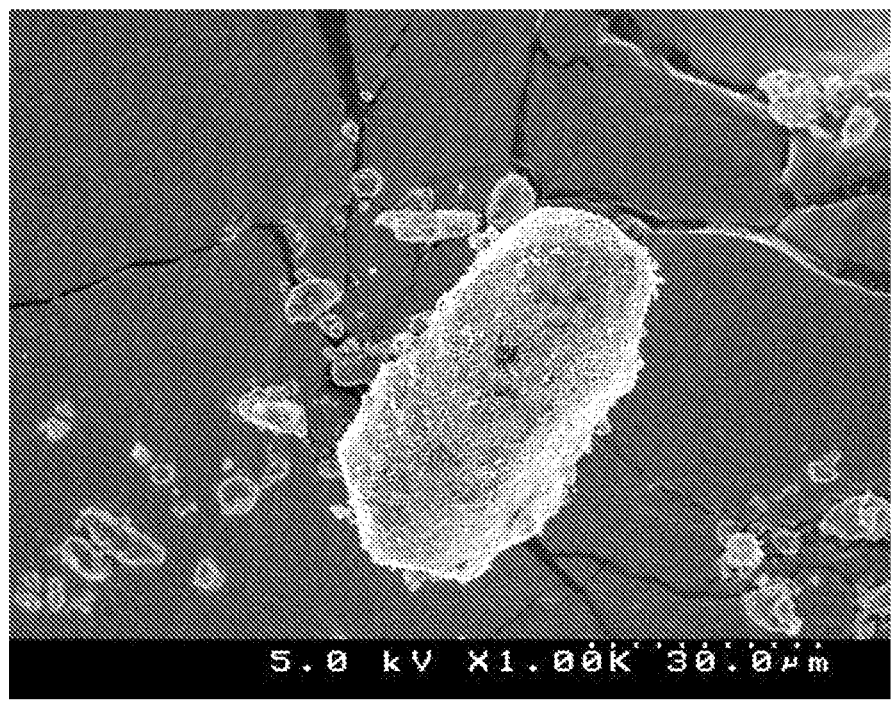
FIG. 19 shows an electron micrograph (1000-fold) of the tolbutamide that is 100% coated with calcium carbonate.
Figure 20:
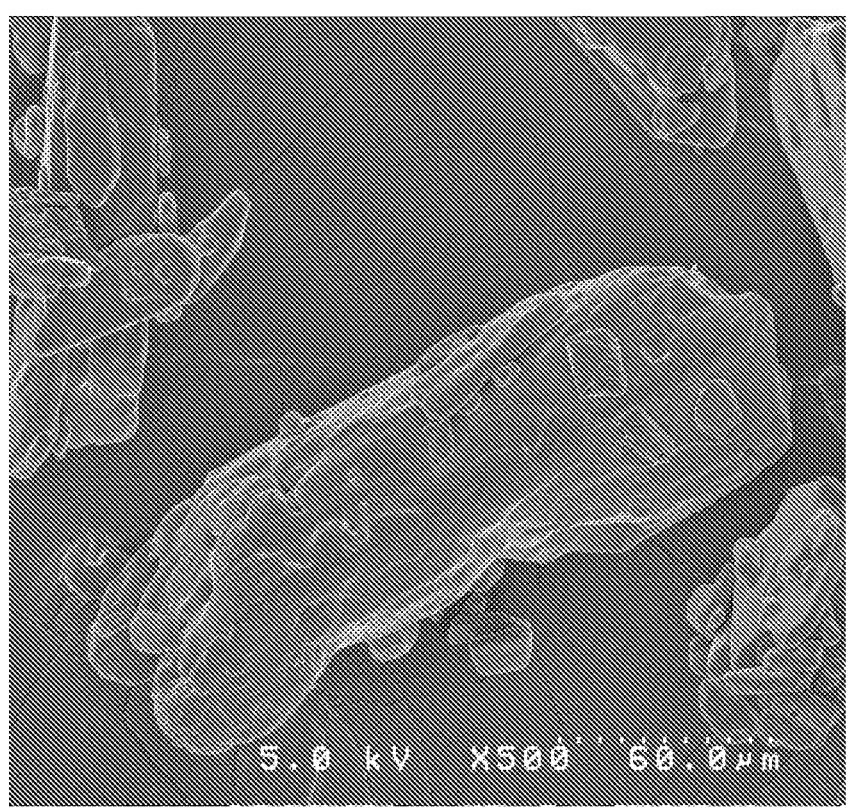
FIG. 20 shows an electron micrograph (500-fold) of the tolbutamide of Comparative Example 7-5.

FIGS. 1 to 19 show electron micrographs of the above-prepared substances with improved aqueous solubility and poorly-soluble substances of the Examples. Observation through an electron microscope was performed using a Field Emission Scanning Electron Microscope S-4500 (manufactured by Hitachi, Ltd.). The magnification used through the observation was adjusted, as appropriate, so that the coating state became clear.

7. Dissolution Test of Poorly-Soluble Substances

A poorly-soluble substance coated with calcium compound microparticles (a substance with improved aqueous solubility) and a test solution (50 mL) were placed in a 50-mL screw cap centrifuge tube made of glass. From initiation of the test, the mixed solution was stirred with a stirrer having a length of 15 mm. The rotation number of the stirrer was 120 rpm, and all of the tests were conducted in a thermostat at 37±0.5° C. Two types of test solutions, namely, distilled water and 2nd fluid for disintegration test (pH 6.8) of the Japanese Pharmacopoeia were used. As such 2nd fluid for disintegration test of the Japanese Pharmacopoeia, a solution prepared by diluting the 10-fold concentration solution of Kanto Kagaku Co., Ltd. with distilled water was used. With regard to the amount of a substance with improved aqueous solubility used in the dissolution test, a preliminary test was carried out on each substance with improved aqueous solubility several times according to the above described method, and the amount of the substance with improved aqueous solubility used in the dissolution test was defined as an amount approximately two times the amount of the substance with improved aqueous solubility dissolved for 360 minutes.

A comparative test was carried out in the same manner as that described above with the exception that a poorly-soluble substance or the like was used in an amount equal to that of a substance with improved aqueous solubility, instead of the substance with improved aqueous solubility.

1 mL of the solution was sampled in an Eppendorf centrifuge tube, 1, 3, 10, 30, 60, 180 and 360 minutes after initiation of the test. The thus sampled solution was centrifuged at 12,000 rpm for 5 minutes. Thereafter, the substance with improved aqueous solubility and calcium compound microparticles, which had not been dissolved in the solution, were removed. In the case of the comparative test, the poorly-soluble substance or the like, which had not been dissolved in the solution, was removed. An aliquot of this supernatant was immediately frozen. The frozen sample was freeze-dried, and it was then used as a sample in the measurement of the amount of the substance with improved aqueous solubility, which had been dissolved in the test solution. The dissolved poorly-soluble substance was measured mainly using a dual wavelength absorption photometer.

Since the dissolved amount of amoxicillin was hardly measured by an extinction method, it was measured by HPLC, basically in accordance with the method of Abreu et al. (L. R. P. de Abreu, R. A. M. Ortiz, S. C. de Castro and J. Pedrazzoli Jr., HPLC determination of amoxicillin comparative bioavailability in healthy volunteers after a single administration, J. Pharm. Pharmaceut. Sci. (www.ualberta.ca/~csps): 6(2): 223-230, 2003). In the case of cisplatin, the amount of platinum was measured with ICP, and the amount of cisplatin was then calculated from the obtained value.

8-1. [Dissolved Amounts of Poorly-Soluble Substances after Dissolution Test for 360 Minutes]

1. Aspirin

TABLE 4

| | Coating method | Coating agent | | | Coating rate | Dissolution test medium | Dissolved amount (μg/ml) |
| | | Ingredient | Grinding | Disperser | | | |
|---|---|---|---|---|---|---|---|
| Example 1-1 | Mechanofusion System | D. (1) Hydroxyapatite | Wet/fine grinding | Sodium citrate | 100% | Distilled water | 36488.6 |
| | | | | | | Second disintegration test medium | 45565.4 |
| Example 1-2 | Mechanofusion System | D. (1) Hydroxyapatite | Wet/fine grinding | Sodium citrate | 5% | Distilled water | 5810.8 |
| | | | | | | Second disintegration test medium | 9665.3 |
| Example 1-3 | Mechanofusion System | D. (2) Tricalcium phosphate | Wet/fine grinding | Sodium citrate | 100% | Distilled water | 26048.6 |
| | | | | | | Second disintegration test medium | 21768.2 |
| Example 1-4 | Mechanofusion System | D. (3) Calcium carbonate | Wet/fine grinding | Sodium citrate | 100% | Distilled water | 23302.3 |
| | | | | | | Second disintegration test medium | 16890.2 |
| Example 1-5 | Mechanofusion System | C. (1) Hydroxyapatite | Wet/fine grinding | Not used | 100% | Distilled water | 33584.4 |
| | | | | | | Second disintegration test medium | 39907.0 |
| Example 1-6 | Mechanofusion System | C. (2) Tricalcium phosphate | Wet/fine grinding | Not used | 100% | Distilled water | 20844.6 |
| | | | | | | Second disintegration test medium | 17861.2 |
| Example 1-7 | Mechanofusion System | C. (3) Calcium carbonate | Wet/fine grinding | Not used | 100% | Distilled water | 21644.1 |
| | | | | | | Second disintegration test medium | 14771.7 |
| Example 1-8 | Hybridization System | D. (1) Hydroxyapatite | Wet/fine grinding | Sodium citrate | 100% | Distilled water | 34073.1 |
| | | | | | | Second disintegration test medium | 45870.5 |
| Example 1-9 | Hybridization System | G. Hydroxyapatite | Wet/fine grinding | Pyrophosphoric acid | 100% | Distilled water | 22474.2 |
| | | | | | | Second disintegration test medium | 20368.2 |
| Example 1-10 | Hybridization System | E. Hydroxyapatite | Wet/moderate grinding | Sodium citrate | 100% | Distilled water | 18995.5 |
| | | | | | | Second disintegration test medium | 19554.0 |
| Example 1-11 | Hybridization System | F. Hydroxyapatite | Wet/not-grinding | Sodium citrate | 100% | Distilled water | 18045.0 |
| | | | | | | Second disintegration test medium | 19886.6 |
| Example 1-12 | Hybridization System | D. (2) Tricalcium phosphate | Wet/fine grinding | Sodium citrate | 100% | Distilled water | 25185.0 |
| | | | | | | Second disintegration test medium | 20251.9 |
| Example 1-13 | Hybridization System | D. (3) Calcium carbonate | Wet/fine grinding | Sodium citrate | 100% | Distilled water | 22045.4 |
| | | | | | | Second disintegration test medium | 16752.6 |
| Example 1-14 | Hybridization System | C. (1) Hydroxyapatite | Wet/fine grinding | Not used | 100% | Distilled water | 32428.2 |
| | | | | | | Second disintegration test medium | 42584.6 |
| Example 1-15 | Hybridization System | A. Hydroxyapatite | Not-grinding | Not used | 100% | Distilled water | 16853.5 |
| | | | | | | Second disintegration test medium | 18346.8 |
| Example 1-16 | Hybridization System | C. (2) Tricalcium phosphate | Wet/fine grinding | Not used | 100% | Distilled water | 22795.7 |
| | | | | | | Second disintegration test medium | 17183.8 |
| Example 1-17 | Hybridization System | C. (3) Tricalcium phosphate | Wet/fine grinding | Not used | 100% | Distilled water | 21865.5 |
| | | | | | | Second disintegration test medium | 14658.7 |
| Comparative Example 1-18 | Coating Pan | D. (1) Hydroxyapatite | Wet/fine grinding | Sodium citrate | 100% | Distilled water | 19747.2 |
| | | | | | | Second disintegration test medium | 20517.4 |
| Comparative Example 1-19 | Coating Pan | D. (2) Tricalcium phosphate | Wet/fine grinding | Sodium citrate | 100% | Distilled water | 13520.8 |
| | | | | | | Second disintegration test medium | 16674.0 |
| Comparative Example 1-20 | Coating Pan | D. (3) Calcium carbonate | Wet/fine grinding | Sodium citrate | 100% | Distilled water | 11481.0 |
| | | | | | | Second disintegration test medium | 12269.0 |
| Comparative Example 1-21 | Coating Pan | C. (1) Hydroxyapatite | Wet/fine grinding | Not used | 100% | Distilled water | 16189.5 |
| | | | | | | Second disintegration test medium | 16712.0 |
| Comparative Example 1-22 | Coating Pan | C. (2) Tricalcium phosphate | Wet/fine grinding | Not used | 100% | Distilled water | 10611.5 |
| | | | | | | Second disintegration test medium | 13472.3 |
| Comparative Example 1-23 | Coating Pan | C. (3) Calcium carbonate | Wet/fine grinding | Not used | 100% | Distilled water | 9429.7 |
| | | | | | | Second disintegration test medium | 11697.1 |
| Comparative Example 1-1 | Hybridization System | Mother nucleus of HAP coated with aspirin | | Not used | 100% | Distilled water | 7159.6 |
| | | | | | | Second disintegration test medium | 7707.0 |

TABLE 4-continued

|  | Coating method | Coating agent | | | Coating rate | Dissolution test medium | Dissolved amount (μg/ml) |
| --- | --- | --- | --- | --- | --- | --- | --- |
|  |  | Ingredient | Grinding | Disperser |  |  |  |
| Comparative Example 1-2 | Hybridization System | Mother nucleus of crystalline cellulose coated with aspirin | | Not used | 100% | Distilled water<br>Second disintegration test medium | 9571.1<br>9827.7 |
| Comparative Example 1-3 |  | Aspirin | | | | Distilled water<br>Second disintegration test medium | 3110.4<br>6552.7 |
| Comparative Example 1-4 |  | Mixing aspirin with "C. (1) Hydroxyapatite microparticle prepared by wet method" with weight 2 times heavier than aspirin | | Not used | | Distilled water<br>Second disintegration test medium | 2512.9<br>1059.5 |

2. Bezafibrate

TABLE 5

|  | Coating method | Coating agent | | | Coating rate | Dissolution test medium | Dissolved amount (μg/ml) |
| --- | --- | --- | --- | --- | --- | --- | --- |
|  |  | Ingredient | Grinding | Disperser |  |  |  |
| Example 2-1 | Mechanofusion System | D. (1) Hydroxyapatite | Wet/fine grinding | Sodium citrate | 100% | Distilled water<br>Second disintegration test medium | 4126.7<br>7288.8 |
| Example 2-2 | Mechanofusion System | D. (1) Hydroxyapatite | Wet/fine grinding | Sodium citrate | 80% | Distilled water<br>Second disintegration test medium | 3440.3<br>6538.0 |
| Example 2-3 | Mechanofusion System | D. (1) Hydroxyapatite | Wet/fine grinding | Sodium citrate | 60% | Distilled water<br>Second disintegration test medium | 1796.6<br>6001.1 |
| Example 2-4 | Mechanofusion System | D. (1) Hydroxyapatite | Wet/fine grinding | Sodium citrate | 10% | Distilled water<br>Second disintegration test medium | 1215.3<br>4080.2 |
| Example 2-5 | Mechanofusion System | C. (1) Hydroxyapatite | Wet/fine grinding | Not used | 100% | Distilled water<br>Second disintegration test medium | 4071.8<br>7177.9 |
| Example 2-6 | Hybridization System | D. (1) Hydroxyapatite | Wet/fine grinding | Sodium citrate | 100% | Distilled water<br>Second disintegration test medium | 4276.9<br>7243.5 |
| Example 2-7 | Hybridization System | B. Hydroxyapatite | Dry/fine grinding | Not used | 100% | Distilled water<br>Second disintegration test medium | 3904.9<br>6667.1 |
| Comparative Example 2-8 | Coating Pan | D. (1) Hydroxyapatite | Wet/fine grinding | Sodium citrate | 100% | Distilled water<br>Second disintegration test medium | 1045.8<br>5015.7 |
| Comparative Example 2-9 | Coating Pan | C. (1) Hydroxyapatite | Wet/fine grinding | Not used | 100% | Distilled water<br>Second disintegration test medium | 904.9<br>4267.1 |
| Comparative Example 2-1 |  | Impregnation of porous hydroxyapatite with bezafibrate | | Not used | | Distilled water<br>Second disintegration test medium | 9.2<br>972.5 |
| Comparative Example 2-2 |  | Commercially available bezafibrate agent | | | | Distilled water<br>Second disintegration test medium | 287.7<br>981.3 |
| Comparative Example 2-3 |  | Bezafibrate | | | | Distilled water<br>Second disintegration test medium | 13.2<br>3096.6 |

3. Chlormadinone Acetate

TABLE 6

|  | Coating method | Coating agent | | | Coating rate | Dissolution test medium | Dissolved amount (μg/ml) |
| --- | --- | --- | --- | --- | --- | --- | --- |
|  |  | Ingredient | Grinding | Disperser |  |  |  |
| Example 3-1 | Mechanofusion System | D. (1) Hydroxyapatite | Wet/fine grinding | Sodium citrate | 100% | Distilled water<br>Second disintegration test medium | 14.6<br>70.7 |
| Example 3-2 | Mechanofusion System | D. (1) Hydroxyapatite | Wet/fine grinding | Sodium citrate | 90% | Distilled water<br>Second disintegration test medium | 13.7<br>64.1 |
| Example 3-3 | Mechanofusion System | D. (1) Hydroxyapatite | Wet/fine grinding | Sodium citrate | 30% | Distilled water<br>Second disintegration test medium | 10.2<br>31.6 |
| Example 3-4 | Mechanofusion System | C. (1) Hydroxyapatite | Wet/fine grinding | Not used | 100% | Distilled water<br>Second disintegration test medium | 10.5<br>59.4 |
| Example 3-5 | Mechanofusion System | C. (1) Hydroxyapatite | Wet/fine grinding | Not used | 30% | Distilled water<br>Second disintegration test medium | 5.6<br>21.0 |
| Example 3-6 | Hybridization System | D. (1) Hydroxyapatite | Wet/fine grinding | Sodium citrate | 100% | Distilled water<br>Second disintegration test medium | 14.2<br>73.0 |

TABLE 6-continued

| | Coating method | Coating agent | | | Coating rate | Dissolution test medium | Dissolved amount (µg/ml) |
|---|---|---|---|---|---|---|---|
| | | Ingredient | Grinding | Disperser | | | |
| Example 3-7 | Hybridization System | B. Hydroxyapatite | Dry/fine grinding | Not used | 100% | Distilled water<br>Second disintegration test medium | 10.3<br>72.7 |
| Comparative Example 3-8 | Coating Pan | D. (1) Hydroxyapatite | Wet/fine grinding | Sodium citrate | 100% | Distilled water<br>Second disintegration test medium | 6.2<br>6.0 |
| Comparative Example 3-9 | Coating Pan | C. (1) Hydroxyapatite | Wet/fine grinding | Not used | 100% | Distilled water<br>Second disintegration test medium | 5.8<br>4.1 |
| Comparative Example 3-1 | Impregnation of porous hydroxyapatite with chlormadinone acetate. | | | Not used | | Distilled water<br>Second disintegration test medium | 0.8<br>0.6 |
| Comparative Example 3-2 | Chlormadinone acetate | | | | | Distilled water<br>Second disintegration test medium | 1.2<br>2.8 |

4. Omeprazole

TABLE 7

| | Coating method | Coating agent | | | Coating rate | Dissolution test medium | Dissolved amount (µg/ml) |
|---|---|---|---|---|---|---|---|
| | | Ingredient | Grinding | Disperser | | | |
| Example 4-1 | Mechanofusion System | D. (1) Hydroxyapatite | Wet/fine grinding | Sodium citrate | 100% | Distilled water<br>Second disintegration test medium | 402.3<br>355.7 |
| Example 4-2 | Mechanofusion System | C. (1) Hydroxyapatite | Wet/fine grinding | Not used | 100% | Distilled water<br>Second disintegration test medium | 375.0<br>320.8 |
| Example 4-3 | Hybridization System | D. (1) Hydroxyapatite | Wet/fine grinding | Sodium citrate | 100% | Distilled water<br>Second disintegration test medium | 395.0<br>353.2 |
| Example 4-4 | Hybridization System | C. (1) Hydroxyapatite | Wet/fine grinding | Not used | 100% | Distilled water<br>Second disintegration test medium | 351.7<br>330.9 |
| Comparative Example 4-5 | Coating Pan | D. (1) Hydroxyapatite | Wet/fine grinding | Sodium citrate | 100% | Distilled water<br>Second disintegration test medium | 303.5<br>294.4 |
| Comparative Example 4-6 | Coating Pan | C. (1) Hydroxyapatite | Wet/fine grinding | Not used | 100% | Distilled water<br>Second disintegration test medium | 297.5<br>267.9 |
| Comparative Example 4-1 | Omeprazole | | | | | Distilled water<br>Second disintegration test medium | 141.6<br>169.9 |

5. Probucol

TABLE 8

| | Coating method | Coating agent | | | Coating rate | Dissolution test medium | Dissolved amount (µg/ml) |
|---|---|---|---|---|---|---|---|
| | | Ingredient | Grinding | Disperser | | | |
| Example 5-1 | Mechanofusion System | D. (1) Hydroxyapatite | Wet/fine grinding | Sodium citrate | 100% | Distilled water<br>Second disintegration test medium | 339.6<br>160.2 |
| Example 5-2 | Mechanofusion System | D. (1) Hydroxyapatite | Wet/fine grinding | Sodium citrate | 70% | Distilled water<br>Second disintegration test medium | 238.0<br>129.5 |
| Example 5-3 | Mechanofusion System | D. (1) Hydroxyapatite | Wet/fine grinding | Sodium citrate | 50% | Distilled water<br>Second disintegration test medium | 116.1<br>108.6 |
| Example 5-4 | Mechanofusion System | D. (1) Hydroxyapatite | Wet/fine grinding | Sodium citrate | 10% | Distilled water<br>Second disintegration test medium | 52.3<br>67.4 |
| Example 5-5 | Mechanofusion System | C. (1) Hydroxyapatite | Wet/fine grinding | Not used | 100% | Distilled water<br>Second disintegration test medium | 260.5<br>138.5 |
| Example 5-6 | Mechanofusion System | C. (1) Hydroxyapatite | Wet/fine grinding | Not used | 10% | Distilled water<br>Second disintegration test medium | 51.5<br>42.6 |
| Example 5-7 | Hybridization System | D. (1) Hydroxyapatite | Wet/fine grinding | Sodium citrate | 100% | Distilled water<br>Second disintegration test medium | 351.4<br>147.7 |
| Example 5-8 | Hybridization System | D. (1) Hydroxyapatite | Wet/fine grinding | Sodium citrate | 50% | Distilled water<br>Second disintegration test medium | 115.0<br>94.8 |
| Example 5-9 | Hybridization System | D. (1) Hydroxyapatite | Wet/fine grinding | Sodium citrate | 10% | Distilled water<br>Second disintegration test medium | 51.6<br>61.1 |

TABLE 8-continued

| | Coating method | Coating agent Ingredient | Grinding | Disperser | Coating rate | Dissolution test medium | Dissolved amount (μg/ml) |
|---|---|---|---|---|---|---|---|
| Example 5-10 | Hybridization System | C. (1) Hydroxyapatite | Wet/fine grinding | Not used | 100% | Distilled water<br>Second disintegration test medium | 342.9<br>114.8 |
| Example 5-11 | Hybridization System | C. (1) Hydroxyapatite | Wet/not-grinding | Not used | 50% | Distilled water<br>Second disintegration test medium | 100.6<br>88.6 |
| Example 5-12 | Hybridization System | C. (1) Hydroxyapatite | Wet/fine grinding | Not used | 10% | Distilled water<br>Second disintegration test medium | 45.5<br>59.9 |
| Comparative Example 5-13 | Coating Pan | D. (1) Hydroxyapatite | Wet/fine grinding | Sodium citrate | 100% | Distilled water<br>Second disintegration test medium | 207.0<br>112.1 |
| Comparative Example 5-14 | Coating Pan | C. (1) Hydroxyapatite | Wet/fine grinding | Not used | 100% | Distilled water<br>Second disintegration test medium | 184.6<br>104.5 |
| Comparative Example 5-1 | Impregnation of porous hydroxyapatite with probucol | | | Not used | | Distilled water<br>Second disintegration test medium | 0.6<br>0.3 |
| Comparative Example 5-2 | Commercially available probucol agent | | | | | Distilled water<br>Second disintegration test medium | 13.8<br>37.8 |
| Comparative Example 5-3 | Probucol | | | | | Distilled water<br>Second disintegration test medium | 9.7<br>28.0 |

6. Triamterene

TABLE 9

| | Coating method | Coating agent Ingredient | Grinding | Disperser | Coating rate | Dissolution test medium | Dissolved amount (μg/ml) |
|---|---|---|---|---|---|---|---|
| Example 6-1 | Mechanofusion System | D. (1) Hydroxyapatite | Wet/fine grinding | Sodium citrate | 100% | Distilled water<br>Second disintegration test medium | 56.6<br>104.5 |
| Example 6-2 | Mechanofusion System | C. (1) Hydroxyapatite | Wet/fine grinding | Not used | 100% | Distilled water<br>Second disintegration test medium | 52.8<br>74.7 |
| Example 6-3 | Hybridization System | D. (1) Hydroxyapatite | Wet/fine grinding | Sodium citrate | 100% | Distilled water<br>Second disintegration test medium | 60.3<br>97.6 |
| Example 6-4 | Hybridization System | C. (1) Hydroxyapatite | Wet/fine grinding | Not used | 100% | Distilled water<br>Second disintegration test medium | 56.3<br>85.9 |
| Comparative Example 6-5 | Coating Pan | D. (1) Hydroxyapatite | Wet/fine grinding | Sodium citrate | 100% | Distilled water<br>Second disintegration test medium | 46.5<br>63.3 |
| Comparative Example 6-6 | Coating Pan | C. (1) Hydroxyapatite | Wet/fine grinding | Not used | 100% | Distilled water<br>Second disintegration test medium | 42.7<br>58.0 |
| Comparative Example 6-1 | Triamterene | | | | | Distilled water<br>Second disintegration test medium | 21.3<br>18.4 |

7. Tobutamide

TABLE 10

| | Coating method | Coating agent Ingredient | Grinding | Disperser | Coating rate | Dissolution test medium | Dissolved amount (μg/ml) |
|---|---|---|---|---|---|---|---|
| Example 7-1 | Mechanofusion System | D. (1) Hydroxyapatite | Wet/fine grinding | Sodium citrate | 100% | Distilled water<br>Second disintegration test medium | 2592.4<br>6913.4 |
| Example 7-2 | Mechanofusion System | C. (1) Hydroxyapatite | Wet/fine grinding | Not used | 100% | Distilled water<br>Second disintegration test medium | 1822.0<br>6432.3 |
| Example 7-3 | Hybridization System | D. (1) Hydroxyapatite | Wet/fine grinding | Sodium citrate | 100% | Distilled water<br>Second disintegration test medium | 2278.3<br>6781.5 |
| Example 7-4 | Hybridization System | C. (1) Hydroxyapatite | Wet/fine grinding | Not used | 100% | Distilled water<br>Second disintegration test medium | 1985.2<br>6569.1 |
| Comparative Example 7-5 | Coating Pan | D. (1) Hydroxyapatite | Wet/fine grinding | Sodium citrate | 100% | Distilled water<br>Second disintegration test medium | 1472.3<br>4989.2 |

TABLE 10-continued

|  | Coating method | Coating agent | | | Coating rate | Dissolution test medium | Dissolved amount (μg/ml) |
|---|---|---|---|---|---|---|---|
|  |  | Ingredient | Grinding | Disperser |  |  |  |
| Comparative Example 7-6 | Coating Pan | C. (1) Hydroxyapatite | Wet/fine grinding | Not used | 100% | Distilled water Second disintegration test medium | 1158.9 4933.1 |
| Comparative Example 7-1 | Hybridization System | Mother nucleus of HAP coated with poorly-soluble ingredient | | Not used | 100% | Distilled water Second disintegration test medium | 243.4 2079.3 |
| Comparative Example 7-2 | Hybridization System | Mother nucleus of crystalline cellulose with poorly-soluble ingredient | | Not used | 100% | Distilled water Second disintegration test medium | 139.3 1457.0 |
| Comparative Example 7-3 | | Impregnation of porous hydroxyapatite with tolbutamide | | Not used | | Distilled water Second disintegration test medium | 48.0 993.3 |
| Comparative Example 7-4 | | Commercially available tolbutamide agent | | | | Distilled water Second disintegration test medium | 73.3 2164.8 |
| Comparative Example 7-5 | | Tolbutamide | | | | Distilled water Second disintegration test medium | 68.6 2449.4 |

8. Amoxicillin

TABLE 11

|  | Coating method | Coating agent | | | Coating rate | Dissolution test medium | Dissolved amount (μg/ml) |
|---|---|---|---|---|---|---|---|
|  |  | Ingredient | Grinding | Disperser |  |  |  |
| Example 8-1 | Mechanofusion System | D. (1) Hydroxyapatite | Wet/fine grinding | Sodium citrate | 100% | Distilled water Second disintegration test medium | 6752.0 15624.3 |
| Example 8-2 | Mechanofusion System | C. (1) Hydroxyapatite | Wet/fine grinding | Not used | 100% | Distilled water Second disintegration test medium | 5659.8 13691.3 |
| Example 8-3 | Hybridization System | D. (1) Hydroxyapatite | Wet/fine grinding | Sodium citrate | 100% | Distilled water Second disintegration test medium | 6992.7 16069.0 |
| Example 8-4 | Hybridization System | C. (1) Hydroxyapatite | Wet/fine grinding | Not used | 100% | Distilled water Second disintegration test medium | 6757.2 14655.8 |
| Comparative Example 8-5 | Coating Pan | D. (1) Hydroxyapatite | Wet/fine grinding | Sodium citrate | 100% | Distilled water Second disintegration test medium | 5719.4 11294.5 |
| Comparative Example 8-6 | Coating Pan | C. (1) Hydroxyapatite | Wet/fine grinding | Not used | 100% | Distilled water Second disintegration test medium | 5016.3 10490.7 |
| Comparative Example 8-1 | | Amoxicillin | | | | Distilled water Second disintegration test medium | 2851.1 6570.8 |

9. Cisplatin

TABLE 12

|  | Coating method | Coating agent | | | Coating rate | Dissolution test medium | Dissolved amount (μg/ml) |
|---|---|---|---|---|---|---|---|
|  |  | Ingredient | Grinding | Disperser |  |  |  |
| Example 9-1 | Mechanofusion System | D. (1) Hydroxyapatite | Wet/fine grinding | Sodium citrate | 100% | Distilled water Second disintegration test medium | 9254.4 14801.3 |
| Example 9-2 | Mechanofusion System | C. (1) Hydroxyapatite | Wet/fine grinding | Not used | 100% | Distilled water Second disintegration test medium | 8529.7 13757.2 |
| Example 9-3 | Hybridization System | D. (1) Hydroxyapatite | Wet/fine grinding | Sodium citrate | 100% | Distilled water Second disintegration test medium | 9651.9 14656.2 |
| Example 9-4 | Hybridization System | C. (1) Hydroxyapatite | Wet/fine grinding | Not used | 100% | Distilled water Second disintegration test medium | 9472.1 13754.6 |
| Comparative Example 9-5 | Coating Pan | D. (1) Hydroxyapatite | Wet/fine grinding | Sodium citrate | 100% | Distilled water Second disintegration test medium | 6378.5 10145.2 |

TABLE 12-continued

| | Coating method | Coating agent Ingredient | Grinding | Disperser | Coating rate | Dissolution test medium | Dissolved amount (μg/ml) |
|---|---|---|---|---|---|---|---|
| Comparative Example 9-6 | Coating Pan | C. (1) Hydroxyapatite | Wet/fine grinding | Not used | 100% | Distilled water<br>Second disintegration test medium | 5847.6<br>9382.1 |
| Comparative Example 9-1 | | Cisplatin | | | | Distilled water<br>Second disintegration test medium | 3722.3<br>4072.4 |

10. Trichlorocarbanilide

TABLE 13

| | Coating method | Coating agent Ingredient | Grinding | Disperser | Coating rate | Dissolution test medium | Dissolved amount (μg/ml) |
|---|---|---|---|---|---|---|---|
| Example 10-1 | Mechanofusion System | D. (1) Hydroxyapatite | Wet/fine grinding | Sodium citrate | 100% | Distilled water<br>Second disintegration test medium | 8.0<br>15.2 |
| Example 10-2 | Mechanofusion System | D. (2) Tricalcium phosphate | Wet/fine grinding | Sodium citrate | 100% | Distilled water<br>Second disintegration test medium | 2.8<br>9.6 |
| Example 10-3 | Mechanofusion System | D. (3) Calcium carbonate | Wet/fine grinding | Sodium citrate | 100% | Distilled water<br>Second disintegration test medium | 3.7<br>9.1 |
| Example 10-4 | Mechanofusion System | C. (1) Hydroxyapatite | Wet/fine grinding | Not used | 100% | Distilled water<br>Second disintegration test medium | 7.0<br>9.8 |
| Example 10-5 | Mechanofusion System | C. (2) Tricalcium phosphate | Wet/fine grinding | Not used | 100% | Distilled water<br>Second disintegration test medium | 2.4<br>7.5 |
| Example 10-6 | Mechanofusion System | C. (3) Calcium carbonate | Wet/fine grinding | Not used | 100% | Distilled water<br>Second disintegration test medium | 2.5<br>8.4 |
| Example 10-7 | Hybridization System | D. (1) Hydroxyapatite | Wet/fine grinding | Sodium citrate | 100% | Distilled water<br>Second disintegration test medium | 8.1<br>14.5 |
| Example 10-8 | Hybridization System | C. (1) Hydroxyapatite | Wet/fine grinding | Not used | 100% | Distilled water<br>Second disintegration test medium | 6.7<br>12.9 |
| Comparative Example 10-9 | Coating Pan | D. (1) Hydroxyapatite | Wet/fine grinding | Sodium citrate | 100% | Distilled water<br>Second disintegration test medium | 5.8<br>10.5 |
| Comparative Example 10-10 | Coating Pan | D. (2) Tricalcium phosphate | Wet/fine grinding | Sodium citrate | 100% | Distilled water<br>Second disintegration test medium | 1.9<br>5.3 |
| Comparative Example 10-11 | Coating Pan | D. (3) Calcium carbonate | Wet/fine grinding | Sodium citrate | 100% | Distilled water<br>Second disintegration test medium | 1.6<br>6.0 |
| Comparative Example 10-12 | Coating Pan | C. (1) Hydroxyapatite | Wet/fine grinding | Not used | 100% | Distilled water<br>Second disintegration test medium | 4.4<br>9.3 |
| Comparative Example 10-13 | Coating Pan | C. (2) Tricalcium phosphate | Wet/fine grinding | Not used | 100% | Distilled water<br>Second disintegration test medium | 1.4<br>5.0 |
| Comparative Example 10-14 | Coating Pan | C. (3) Calcium carbonate | Wet/fine grinding | Not used | 100% | Distilled water<br>Second disintegration test medium | 1.5<br>5.2 |
| Comparative Example 10-1 | | Trichlorocarbanilide | | | | Distilled water<br>Second disintegration test medium | 0.6<br>1.5 |

11. Glibenclamide

TABLE 14

| | Coating method | Coating agent Ingredient | Grinding | Disperser | Coating rate | Dissolution test medium | Dissolved amount (μg/ml) |
|---|---|---|---|---|---|---|---|
| Example 11 | Mechanofusion System | D. (1) Hydroxyapatite | Wet/fine grinding | Sodium citrate | 100% | Distilled water<br>Second disintegration test medium | 18.8<br>81.8 |
| Comparative Example 11 | | Glibenclamide | | | | Distilled water<br>Second disintegration test medium | 6.4<br>8.0 |

12. Atenolol

TABLE 15

| | Coating method | Coating agent | | | Coating rate | Dissolution test medium | Dissolved amount (μg/ml) |
|---|---|---|---|---|---|---|---|
| | | Ingredient | Grinding | Disperser | | | |
| Example 12 | Mechanofusion System | D. (1) Hydroxyapatite | Wet/fine grinding Atenolol | Sodium citrate | 100% | Distilled water<br>Second disintegration test medium | 50215.5<br>55239.4 |
| Comparative Example 12 | | | | | | Distilled water<br>Second disintegration test medium | 20566.2<br>18076.2 |

13. Trimethoprim

TABLE 16

| | Coating method | Coating agent | | | Coating rate | Dissolution test medium | Dissolved amount (μg/ml) |
|---|---|---|---|---|---|---|---|
| | | Ingredient | Grinding | Disperser | | | |
| Example 13 | Mechanofusion System | D. (1) Hydroxyapatite | Wet/fine grinding Trimethoprim | Sodium citrate | 100% | Distilled water<br>Second disintegration test medium | 1712.6<br>3532.6 |
| Comparative Example 13 | | | | | | Distilled water<br>Second disintegration test medium | 656.3<br>1321.9 |

14. Primidone

TABLE 17

| | Coating method | Coating agent | | | Coating rate | Dissolution test medium | Dissolved amount (μg/ml) |
|---|---|---|---|---|---|---|---|
| | | Ingredient | Grinding | Disperser | | | |
| Example 14 | Mechanofusion System | D. (1) Hydroxyapatite | Wet/fine grinding Primidone | Sodium citrate | 100% | Distilled water<br>Second disintegration test medium | 388.9<br>724.3 |
| Comparative Example 14 | | | | | | Distilled water<br>Second disintegration test medium | 180.3<br>335.2 |

8-2. [Dissolution Time and Dissolved Amount]

In the case of Examples regarding which no coating methods are described in the coating ingredient column, the coating treatment was carried out according to the Mechanofusion System, using "D. (1) Hydroxyapatite microparticles with surface coated with dispersing agent." Moreover, in Comparative Examples 15 to 49, poorly-soluble substances themselves (not coated) were used.

1. Aspirin

Dissolution test using water Dissolved amount (μg/ml)

TABLE 18

| Example No. | Coating ingredient | Elution time (min) | | | | | | |
|---|---|---|---|---|---|---|---|---|
| | | 1 | 3 | 10 | 30 | 60 | 180 | 360 |
| Example 1-1 | Hydroxyapatite | 36215.7 | 36231.0 | 36233.5 | 36236.1 | 36488.6 | 36496.2 | 36531.9 |
| Example 1-3 | Tricalcium phosphate | 22351.4 | 23110.5 | 24206.2 | 25330.4 | 25336.5 | 26473.4 | 26048.6 |
| Example 1-4 | Calcium carbonate | 21235.3 | 22092.3 | 22300.4 | 22520.8 | 23002.3 | 23302.3 | 23638.9 |
| Comparative Example 1-1 | Mother nucleus of HAP coated with aspirin | 2168.4 | 3344.5 | 4706.9 | 5058.8 | 5947.8 | 6452.2 | 7159.6 |
| Comparative Example 1-2 | Mother nucleus of crystalline cellulose coated with aspirin | 1459.2 | 3171.9 | 4995.0 | 6777.8 | 8862.2 | 9326.0 | 9571.1 |
| Comparative Example 1-3 | — | 1831.9 | 2934.9 | 2985.3 | 3084.0 | 3105.7 | 3108.1 | 3110.4 |

TABLE 18-continued

| Example No. | Coating ingredient | Elution time (min) | | | | | | |
|---|---|---|---|---|---|---|---|---|
| | | 1 | 3 | 10 | 30 | 60 | 180 | 360 |
| Comparative Example 1-4 | Mixture of aspirin and hydroxyapatite microparticle | 16.6 | 82.5 | 250.7 | 1297.5 | 2166.7 | 2441.0 | 2512.9 |

Dissolution test using 2nd fluid for disintegration test Dissolved amount (μg/ml)

TABLE 19

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 1-1 | Hydroxyapatite | 32031.5 | 36204.8 | 41955.6 | 42908.8 | 44983.4 | 45186.3 | 45585.4 |
| Example 1-2 | Tricalcium phosphate | 15281.8 | 17854.1 | 19306.5 | 19378.6 | 19904.6 | 21311.7 | 21768.2 |
| Example 1-3 | Calcium carbonate | 15557.9 | 16011.8 | 16011.8 | 16318.9 | 16332.2 | 16388.3 | 16890.2 |
| Comparative Example 1-1 | Mother nucleus of HAP coated with aspirin | 1662.7 | 2579.1 | 3788.3 | 5018.3 | 6145.0 | 7121.0 | 7707.0 |
| Comparative Example 1-2 | Mother nucleus of crystalline cellulose coated with aspirin | 5052.7 | 6199.3 | 7061.8 | 8341.7 | 8853.3 | 9341.7 | 9827.7 |
| Comparative Example 1-3 | — | 252.7 | 1020.4 | 5352.3 | 5963.6 | 6289.8 | 6458.1 | 8552.7 |
| Comparative Example 1-4 | Mixture of aspirin and hydroxyapatite microparticle | 39.0 | 98.0 | 205.9 | 226.3 | 328.2 | 471.9 | 1059.5 |

2. Bezafibrate

Dissolution test using water Dissolved amount (μg/ml)

TABLE 20

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 2-1 | Coating rate · 100% | 3079.7 | 3338.1 | 3585.4 | 3708.2 | 3874.0 | 3981.4 | 4120.7 |
| Example 2-2 | Coating rate · 80% | 2758.5 | 2941.9 | 3161.9 | 3289.5 | 3336.4 | 3392.2 | 3440.3 |
| Example 2-3 | Coating rate · 60% | 1501.2 | 1588.0 | 1663.5 | 1667.4 | 1737.1 | 1766.6 | 1706.6 |
| Example 2-4 | Coating rate · 10% | 71.4 | 182.1 | 468.3 | 621.3 | 825.4 | 1083.4 | 1215.3 |
| Comparative Example 2-8 | Hydroxyapatite with disperser/100% coating pan | 74.8 | 191.5 | 408.1 | 530.2 | 772.5 | 907.2 | 1045.8 |
| Comparative Example 2-9 | Hydroxyapatite without disperser/100% coating pan | 0.0 | 104.4 | 290.4 | 480.2 | 615.7 | 776.9 | 904.9 |
| Comparative Example 2-1 | Porous hydroxyapatite impregnated with bezafibrate | 0.0 | 0.0 | 1.6 | 2.9 | 4.1 | 6.1 | 9.2 |
| Comparative Example 2-2 | Commercially available agent | 0.0 | 0.0 | 2.1 | 28.3 | 44.0 | 71.4 | 287.7 |
| Comparative Example 2-3 | — | 10.4 | 10.9 | 11.6 | 11.9 | 12.3 | 12.9 | 13.2 |

Dissolution test using 2nd fluid disintegration test Dissolved amount (μg/ml)

TABLE 21

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 2-1 | Coating rate · 100% | 5395.2 | 5840.9 | 6014.0 | 6391.4 | 6509.8 | 6773.5 | 7288.8 |
| Example 2-2 | Coating rate · 80% | 4840.4 | 5419.9 | 5773.4 | 5840.2 | 5976.7 | 6107.3 | 6538.0 |
| Example 2-3 | Coating rate · 60% | 4345.4 | 5154.8 | 5528.5 | 5584.1 | 5595.6 | 5683.8 | 6001.1 |
| Example 2-4 | Coating rate · 10% | 2679.7 | 3164.5 | 3472.8 | 3668.8 | 3857.0 | 4001.5 | 4080.2 |
| Comparative Example 2-8 | Hydroxyapatite with disperser/100% coating pan | 2101.8 | 3271.4 | 3510.2 | 3858.4 | 4244.2 | 4748.6 | 5015.7 |
| Comparative Example 2-9 | Hydroxyapatite without disperser/100% coating pan | 2030.3 | 3331.8 | 3629.6 | 3688.8 | 3851.3 | 4149.8 | 4267.1 |
| Comparative Example 2-1 | Porous hydroxyapatite impregnated with bezafibrate | 0.0 | 29.5 | 355.1 | 450.9 | 492.6 | 681.5 | 972.5 |

TABLE 21-continued

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Comparative Example 2-2 | Commercially available agent | 0.0 | 14.7 | 430.4 | 839.0 | 701.2 | 999.5 | 981.3 |
| Comparative Example 2-3 | — | 805.1 | 2552.5 | 2866.5 | 2942.6 | 2965.5 | 3031.4 | 3096.6 |

3. Chlormadinone Acetate
Dissolution test using water Dissolved amount (μg/ml)

TABLE 22

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 3-1 | Multilayer | 5.0 | 7.4 | 9.6 | 12.8 | 13.1 | 14.4 | 14.4 |
| Example 3-2 | Coating rate · 100% | 2.5 | 7.5 | 11.2 | 13.0 | 13.6 | 14.1 | 14.6 |
| Example 3-3 | Coating rate · 90% | 3.1 | 7.3 | 10.4 | 12.1 | 12.8 | 13.5 | 13.7 |
| | Coating rate · 30% | 1.1 | 2.9 | 5.2 | 7.9 | 9.3 | 9.6 | 10.2 |
| Comparative Example 3-8 | Hydroxyapatite with disperser/100% coating pan | 5.2 | 5.2 | 5.2 | 5.3 | 5.9 | 6.0 | 6.2 |
| Comparative Example 3-9 | Hydroxyapatite with disperser/100% coating pan | 5.3 | 5.4 | 5.6 | 5.6 | 5.7 | 5.7 | 5.8 |
| Comparative Example 3-1 | Porous hydroxyapatite impregnated with chlormadinone acetate | 0.0 | 0.0 | 0.2 | 0.3 | 0.4 | 0.5 | 0.8 |
| Comparative Example 3-2 | | 0.6 | 0.6 | 0.7 | 0.9 | 1.0 | 1.1 | 1.2 |

Dissolution test using 2nd fluid for disintegration test Dissolved amount (μg/ml)

TABLE 23

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 3-1 | Coating rate · 100% | 36.9 | 44.4 | 50.5 | 55.7 | 63.9 | 64.9 | 70.7 |
| Example 3-2 | Coating rate · 90% | 31.3 | 40.7 | 45.2 | 52.6 | 58.6 | 62.5 | 64.1 |
| Example 3-3 | Coating rate · 30% | 7.4 | 12.3 | 22.5 | 25.0 | 29.2 | 30.7 | 31.6 |
| Comparative Example 3-8 | With use of disperser/100% coating pan | 4.1 | 4.6 | 4.7 | 5.1 | 5.1 | 5.3 | 6.0 |
| Comparative Example 3-9 | Without use of disperser/100% coating pan | 2.2 | 2.4 | 2.5 | 2.7 | 2.7 | 3.1 | 4.1 |
| Comparative Example 3-1 | Porous hydroxyapatite impregnated with chlormadinone acetate | 0 | 0 | 0 | 0 | 0 | 0.6 | 0.6 |
| Comparative Example 3-2 | — | 1.4 | 1.4 | 1.8 | 1.0 | 1.0 | 2.3 | 2.8 |

5. Probucol
Dissolution test using water Dissolved amount (μg/ml)

TABLE 24

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 5-1 | Coating rate · 100% | 215.4 | 260.6 | 283.5 | 295.1 | 309.4 | 330.8 | 339.6 |
| Example 5-2 | Coating rate · 70% | 148.0 | 171.9 | 206.4 | 215.3 | 232.9 | 237.7 | 238.0 |
| Example 5-3 | Coating rate · 50% | 78.7 | 79.2 | 95.5 | 102.2 | 106.2 | 111.7 | 116.1 |
| Example 5-4 | Coating rate · 10% | 23.7 | 26.0 | 33.8 | 41.7 | 43.1 | 47.5 | 52.3 |
| Comparative Example 5-1 | Porous hydroxyapatite impregnated with probucol | 0.1 | 0.1 | 0.2 | 0.2 | 0.3 | 0.4 | 0.6 |
| Comparative Example 5-2 | Commercially available agent | 2.7 | 3.5 | 5.9 | 7.9 | 9.8 | 11.7 | 13.8 |
| Comparative Example 5-3 | — | 0.7 | 2.7 | 3.7 | 6.1 | 7.6 | 8.3 | 9.7 |

Dissolution test using 2nd fluid for disintegration test Dissolved amount (μg/ml)

TABLE 25

| Example No. | Coating ingredient Hydroxyapatite | Elution time (min) | | | | | | |
|---|---|---|---|---|---|---|---|---|
| | | 1 | 3 | 10 | 30 | 60 | 180 | 360 |
| Example 5-1 | Coating rate · 100% | 104.8 | 120.3 | 125.6 | 135.2 | 144.6 | 153.5 | 160.2 |
| Example 5-2 | Coating rate · 70% | 80.0 | 84.0 | 96.8 | 107.2 | 112.3 | 123.4 | 129.5 |
| Example 5-3 | Coating rate · 50% | 15.0 | 49.9 | 81.2 | 90.2 | 95.5 | 101.8 | 108.6 |
| Example 5-4 | Coating rate · 10% | 10.2 | 25.8 | 41.9 | 53.3 | 59.8 | 62.1 | 67.4 |
| Comparative Example 5-1 | Porous hydroxyapatite impregnated with probucol | 0.1 | 0.1 | 0.1 | 0.2 | 0.2 | 0.2 | 0.3 |
| Comparative Example 5-2 | Commercially available agent | 2.1 | 12.6 | 20.0 | 27.4 | 31.1 | 32.0 | 37.8 |
| Comparative Example 5-3 | — | 4.7 | 14.9 | 19.9 | 21.2 | 21.8 | 26.8 | 28.0 |

7. Tolbutamide
Dissolution test using water Dissolved amount (μg/ml)

TABLE 26

| Example No. | Coating ingredient | Elution time (min) | | | | | | |
|---|---|---|---|---|---|---|---|---|
| | | 1 | 3 | 10 | 30 | 60 | 180 | 360 |
| Example 7-1 | Hydroxyapatite | 2114.6 | 2421.2 | 2559.5 | 2574.2 | 2584.0 | 2591.9 | 2592.4 |
| Comparative Example 7-1 | Mother nucleus of HAP coated with tolbutamide | 0.0 | 63.4 | 98.4 | 136.2 | 174.8 | 204.6 | 243.4 |
| Comparative Example 7-2 | Mother nucleus of crystalline cellulose coated with tolbutamide | 29.0 | 48.8 | 63.9 | 77.2 | 93.5 | 126.4 | 139.3 |
| Comparative Example 7-3 | Porous hydroxyapatite impregnated with tolbutamide | 14.8 | 17.3 | 29.4 | 31.8 | 38.3 | 43.4 | 48.0 |
| Comparative Example 7-4 | Commercially available agent | 0.0 | 0.0 | 42.0 | 65.9 | 66.0 | 69.4 | 73.3 |
| Comparative Example 7-5 | — | 48.8 | 49.3 | 50.5 | 51.3 | 52.9 | 56.6 | 68.6 |

Dissolution test using 2nd fluid for disintegration test Dissolved amount (μg/ml)

TABLE 27

| Example No. | Coating ingredient | Elution time (min) | | | | | | |
|---|---|---|---|---|---|---|---|---|
| | | 1 | 3 | 10 | 30 | 60 | 180 | 360 |
| Example 7-1 | Hydroxyapatite | 5803.0 | 5015.4 | 6285.2 | 6428.8 | 6654.5 | 6007.2 | 6013.4 |
| Comparative Example 7-1 | Mother nucleus of HAP coated with tolbutamide | 0.0 | 37.7 | 188.5 | 602.3 | 858.7 | 1487.9 | 2079.3 |
| Comparative Example 7-2 | Mother nucleus of crystalline cellulose coated with tolbutamide | 123.8 | 139.5 | 246.1 | 348.3 | 584.7 | 1042.0 | 1457.0 |
| Comparative Example 7-3 | Porous hydroxyapatite impregnated with tolbutamide | 83.9 | 105.7 | 402.3 | 534.4 | 580.2 | 733.4 | 993.3 |
| Comparative Example 7-4 | Commercially available agent | 194.2 | 539.0 | 1286.0 | 1670.5 | 1914.9 | 2136.7 | 2164.8 |
| Comparative Example 7-5 | — | 637.3 | 1597.2 | 2041.9 | 2141.1 | 2429.1 | 2432.9 | 2449.4 |

10. Trichlorocarbanilide

Dissolution test using water Dissolved amount (μg/ml)

TABLE 28

| Example No. | Coating ingredient | Elution time (min) | | | | | | |
|---|---|---|---|---|---|---|---|---|
| | | 1 | 3 | 10 | 30 | 60 | 180 | 360 |
| Example 10-1 | Hydroxyapatite | 2.9 | 3.7 | 4.7 | 5.8 | 6.4 | 7.0 | 8.0 |
| Example 10-2 | Tricalcium phosphate | 1.4 | 1.8 | 1.9 | 2.3 | 2.5 | 2.7 | 2.8 |
| Example 10-3 | Calcium carbonate | 1.0 | 2.4 | 2.8 | 3.0 | 3.4 | 3.6 | 3.7 |
| Comparative Example 10-1 | — | 0.0 | 0.1 | 0.4 | 0.4 | 0.4 | 0.5 | 0.6 |

Dissolution test using 2nd fluid for disintegration test Dissolved amount (μg/ml)

TABLE 29

| Example No. | Coating ingredient | Elution time (min) | | | | | | |
|---|---|---|---|---|---|---|---|---|
| | | 1 | 3 | 10 | 30 | 60 | 180 | 360 |
| Example 10-1 | Hydroxyapatite | 9.7 | 12.4 | 13.3 | 13.7 | 14.3 | 14.6 | 15.2 |
| Example 10-2 | Tricalcium phosphate | 6.1 | 6.9 | 8.0 | 8.7 | 9.0 | 9.4 | 9.6 |
| Example 10-3 | Calcium carbonate | 5.3 | 6.5 | 7.2 | 8.1 | 8.8 | 8.9 | 9.1 |
| Comparative Example 10-1 | — | 0.0 | 0.3 | 0.6 | 0.8 | 1.1 | 1.3 | 1.5 |

11. Theophylline

Dissolution test using water Dissolved amount (μg/ml)

TABLE 30

| Example No. | Elution time (min) | | | | | | |
|---|---|---|---|---|---|---|---|
| | 1 | 3 | 10 | 30 | 60 | 180 | 360 |
| Example 15 | 10084.1 | 12873.5 | 12898.7 | 12955.0 | 12968.2 | 13102.8 | 13019.8 |
| Comparative Example 15 | 7082.2 | 7897.9 | 8554.7 | 8621.6 | 8652.4 | 8672.3 | 8691.5 |

Dissolution test using 2nd fluid for disintegration test Dissolved amount (μg/ml)

TABLE 31

| Example No. | Elution time (min) | | | | | | |
|---|---|---|---|---|---|---|---|
| | 1 | 3 | 10 | 30 | 60 | 180 | 360 |
| Example 15 | 8141.5 | 8847.9 | 8948.2 | 10580.9 | 10605.6 | 10555.5 | 10475.2 |
| Comparative Example 15 | 8133.8 | 8635.7 | 8596.0 | 8929.7 | 9096.5 | 8906.5 | 8906.2 |

12. Ammonium Glycyrrhizinate
Dissolution test using water Dissolved amount (μg/ml)

TABLE 32

| Example No. | Elution time (min) | | | | | | |
| --- | --- | --- | --- | --- | --- | --- | --- |
| | 1 | 3 | 10 | 30 | 60 | 180 | 360 |
| Example 16 | 15197.9 | 15201.8 | 15310.8 | 15396.5 | 15567.2 | 15814.1 | 15745.9 |
| Comparative Example 16 | 2668.0 | 4621.4 | 5945.2 | 6792.2 | 7374.5 | 8826.1 | 8948.1 |

Dissolution test using 2nd fluid for disintegration test Dissolved amount (μg/ml)

TABLE 33

| Example No. | Elution time (min) | | | | | | |
| --- | --- | --- | --- | --- | --- | --- | --- |
| | 1 | 3 | 10 | 30 | 60 | 180 | 360 |
| Example 16 | 15314.8 | 15438.6 | 15477.1 | 15647.8 | 15692.2 | 15719.9 | 15692.2 |
| Comparative Example 16 | 5113.7 | 7012.3 | 9096.3 | 9673.9 | 10149.0 | 10469.7 | 10534.3 |

13. Famotidine
Dissolution test using water Dissolved amount (μg/ml)

TABLE 34

| Example No. | Elution time (min) | | | | | | |
| --- | --- | --- | --- | --- | --- | --- | --- |
| | 1 | 3 | 10 | 30 | 60 | 180 | 360 |
| Example 17 | 1080.2 | 1269.9 | 1816.6 | 2034.8 | 2019.8 | 1978.1 | 1921.5 |
| Comparative Example 17 | 1162.9 | 1416.8 | 1502.6 | 1566.8 | 1565.8 | 1509.8 | 1497.4 |

Dissolution test using 2nd fluid for disintegration test Dissolved amount (μg/ml)

TABLE 35

| Example No. | Elution time (min) | | | | | | |
| --- | --- | --- | --- | --- | --- | --- | --- |
| | 1 | 3 | 10 | 30 | 60 | 180 | 360 |
| Example 17 | 1943.5 | 2409.8 | 2648.0 | 2758.9 | 2790.2 | 2857.9 | 2898.4 |
| Comparative Example 17 | 1980.2 | 2286.6 | 2541.7 | 2600.9 | 2667.9 | 2509.7 | 2410.4 |

14. Sulfamethoxazole
Dissolution test using water Dissolved amount (μg/ml)

TABLE 36

| Example No. | Elution time (min) | | | | | | |
| --- | --- | --- | --- | --- | --- | --- | --- |
| | 1 | 3 | 10 | 30 | 60 | 180 | 360 |
| Example 18 | 2691.3 | 2890.4 | 2937.8 | 3075.1 | 3037.0 | 3002.1 | 2979.4 |
| Comparative Example 18 | 407.4 | 431.6 | 452.6 | 492.1 | 490.0 | 488.1 | 487.0 |

Dissolution test using 2nd fluid for disintegration test Dissolved amount (μg/ml)

TABLE 37

| Example No. | Elution time (min) | | | | | | |
|---|---|---|---|---|---|---|---|
| | 1 | 3 | 10 | 30 | 60 | 180 | 360 |
| Example 18 | 3348.2 | 3380.4 | 3497.6 | 3866.0 | 3868.1 | 3468.4 | 3409.4 |
| Comparative Example 18 | 2588.4 | 2860.3 | 2993.4 | 3151.6 | 3212.3 | 2966.2 | 2794.8 |

15. Cimetidine

Dissolution test using water Dissolved amount (μg/ml)

TABLE 38

| Example No. | Elution time (min) | | | | |
|---|---|---|---|---|---|
| | 3 | 10 | 30 | 120 | 360 |
| Example 19 | 10424.3 | 12636.1 | 12313.3 | 11801.0 | 11579.6 |
| Comparative Example 19 | 6770.2 | 8160.2 | 7564.5 | 7898.3 | 7166.4 |

Dissolution test using 2nd fluid for disintegration test Dissolved amount (μg/ml)

TABLE 39

| Example No. | Elution time (min) | | | | |
|---|---|---|---|---|---|
| | 3 | 10 | 30 | 120 | 360 |
| Example 19 | 9107.1 | 12013.1 | 12391.0 | 11666.6 | 11426.1 |
| Comparative Example 19 | 8676.7 | 10921.2 | 11139.3 | 9475.2 | 8810.0 |

16. Indomethacin

Dissolution test using water Dissolved amount (μg/ml)

TABLE 40

| Example No. | Elution time (min) | | | | |
|---|---|---|---|---|---|
| | 3 | 10 | 30 | 120 | 360 |
| Example 20 | 2406.7 | 1754.5 | 1689.9 | 1678.3 | 1664.0 |
| Comparative Example 20 | 7.8 | 7.9 | 8.0 | 8.5 | 8.2 |

Dissolution test using 2nd fluid for disintegration test Dissolved amount (μg/ml)

TABLE 41

| Example No. | Elution time (min) | | | | |
|---|---|---|---|---|---|
| | 3 | 10 | 30 | 120 | 360 |
| Example 20 | 4670.4 | 3698.0 | 3730.3 | 3903.0 | 3572.2 |
| Comparative Example 20 | 627.9 | 693.7 | 821.8 | 928.5 | 1114.4 |

17. Phenyloin

Dissolution test using water Dissolved amount (μg/ml)

TABLE 42

| Example No. | Elution time (min) | | | | |
|---|---|---|---|---|---|
| | 3 | 10 | 30 | 120 | 360 |
| Example 21 | 470.7 | 595.4 | 598.5 | 542.6 | 470.1 |
| Comparative Example 21 | 26.5 | 23.3 | 23.7 | 23.7 | 24.1 |

Dissolution test using 2nd fluid for disintegration test Dissolved amount (μg/ml)

TABLE 43

| Example No. | Elution time (min) | | | | |
|---|---|---|---|---|---|
| | 3 | 10 | 30 | 120 | 360 |
| Example 21 | 44.4 | 46.7 | 113.3 | 74.7 | 75.5 |
| Comparative Example 21 | 17.4 | 42.1 | 50.7 | 27.2 | 32.5 |

18. Carbamazepine

Dissolution test using water Dissolved amount (μg/ml)

TABLE 44

| Example No. | Elution time (min) | | | | |
|---|---|---|---|---|---|
| | 3 | 10 | 30 | 120 | 360 |
| Example 22 | 309.2 | 396.0 | 445.3 | 307.3 | 322.9 |
| Comparative Example 22 | 291.2 | 234.8 | 214.3 | 159.5 | 153.0 |

Dissolution test using 2nd fluid for disintegration test Dissolved amount (μg/ml)

TABLE 45

| Example No. | Elution time (min) | | | | |
|---|---|---|---|---|---|
| | 3 | 10 | 30 | 120 | 360 |
| Example 22 | 212.8 | 269.0 | 346.8 | 552.1 | 447.3 |
| Comparative Example 22 | 346.6 | 352.2 | 413.9 | 282.1 | 199.3 |

19. Acetazolamide

Dissolution test using water Dissolved amount (μg/ml)

TABLE 46

| | Elution time (min) | | | | |
|---|---|---|---|---|---|
| Example No. | 3 | 10 | 30 | 120 | 360 |
| Example 23 | 1922.0 | 2037.4 | 2620.3 | 3544.7 | 3317.2 |
| Comparative Example 23 | 1040.6 | 1238.7 | 1244.8 | 1251.4 | 1212.0 |

Dissolution test using 2nd fluid for disintegration test Dissolved amount (μg/ml)

TABLE 47

| | Elution time (min) | | | | |
|---|---|---|---|---|---|
| Example No. | 3 | 10 | 30 | 120 | 360 |
| Example 23 | 2094.3 | 2214.2 | 2264.4 | 2296.9 | 2178.2 |
| Comparative Example 23 | 1331.6 | 1662.3 | 1681.5 | 1721.6 | 1654.9 |

20. Alacepril

Dissolution test using water Dissolved amount (μg/ml)

TABLE 48

| | Elution time (min) | | | | |
|---|---|---|---|---|---|
| Example No. | 3 | 10 | 30 | 120 | 360 |
| Example 24 | 17692.5 | 20039.6 | 20574.9 | 21218.6 | 21532.0 |
| Comparative Example 24 | 526.2 | 805.6 | 931.2 | 994.9 | 996.5 |

Dissolution test using 2nd fluid for disintegration test Dissolved amount (μg/ml)

TABLE 49

| | Elution time (min) | | | | |
|---|---|---|---|---|---|
| Example No. | 3 | 10 | 30 | 120 | 360 |
| Example 24 | 22137.5 | 22340.2 | 22501.2 | 23407.9 | 23524.9 |
| Comparative Example 24 | 2311.1 | 2514.7 | 2525.0 | 2588.4 | 2548.2 |

21. Tinidazole

Dissolution test using water Dissolved amount (μg/ml)

TABLE 50

| | Elution time (min) | | | | |
|---|---|---|---|---|---|
| Example No. | 3 | 10 | 30 | 120 | 360 |
| Example 25 | 10417.7 | 12250.8 | 11840.4 | 11822.9 | 11049.0 |
| Comparative Example 25 | 2973.2 | 3880.0 | 4558.1 | 6034.2 | 6207.6 |

Dissolution test using 2nd fluid for disintegration test Dissolved amount (μg/ml)

TABLE 51

| | Elution time (min) | | | | |
|---|---|---|---|---|---|
| Example No. | 3 | 10 | 30 | 120 | 360 |
| Example 25 | 8151.2 | 10205.1 | 9847.6 | 9503.2 | 9195.4 |
| Comparative Example 25 | 4613.3 | 5425.9 | 5825.0 | 7003.0 | 6133.3 |

22. Naproxen

Dissolution test using water Dissolved amount (μg/ml)

TABLE 52

| | Elution time (min) | | | | |
|---|---|---|---|---|---|
| Example No. | 3 | 10 | 30 | 120 | 360 |
| Example 26 | 2276.9 | 2301.8 | 2425.1 | 2383.4 | 2246.2 |
| Comparative Example 26 | 86.6 | 103.8 | 110.5 | 120.8 | 121.8 |

Dissolution test using 2nd fluid for disintegration test Dissolved amount (μg/ml)

TABLE 53

| | Elution time (min) | | | | |
|---|---|---|---|---|---|
| Example No. | 3 | 10 | 30 | 120 | 360 |
| Example 26 | 4666.8 | 5051.7 | 5020.3 | 4743.8 | 4618.2 |
| Comparative Example 26 | 2035.1 | 2270.0 | 2425.8 | 2429.6 | 2450.5 |

23. Norfloxacin

Dissolution test using water Dissolved amount (μg/ml)

TABLE 54

| | Elution time (min) | | | | |
|---|---|---|---|---|---|
| Example No. | 3 | 10 | 30 | 120 | 360 |
| Example 27 | 1947.5 | 1829.3 | 1586.8 | 1306.2 | 1141.7 |
| Comparative Example 27 | 455.9 | 523.1 | 492.3 | 470.7 | 395.5 |

Dissolution test using 2nd fluid for disintegration test Dissolved amount (μg/ml)

TABLE 55

| | Elution time (min) | | | | |
|---|---|---|---|---|---|
| Example No. | 3 | 10 | 30 | 120 | 360 |
| Example 27 | 1515.4 | 1311.8 | 1294.0 | 1255.8 | 1118.6 |
| Comparative Example 27 | 688.7 | 767.1 | 744.1 | 721.6 | 694.7 |

24. Erythromycin

Dissolution test using water Dissolved amount (μg/ml)

TABLE 56

| | Elution time (min) | | | | |
|---|---|---|---|---|---|
| Example No. | 3 | 10 | 30 | 120 | 360 |
| Example 28 | 14822.4 | 3811.9 | 3478.3 | 3435.7 | 3753.9 |
| Comparative Example 28 | 635.0 | 861.6 | 944.7 | 927.7 | 846.1 |

Dissolution test using 2nd fluid for disintegration test Dissolved amount (μg/ml)

TABLE 57

| | Elution time (min) | | | | |
|---|---|---|---|---|---|
| Example No. | 3 | 10 | 30 | 120 | 360 |
| Example 28 | 29402.7 | 16473.8 | 16323.8 | 16821.4 | 18128.5 |
| Comparative Example 28 | 2556.3 | 4984.2 | 5103.6 | 5904.1 | 6044.7 |

25. Epinephrine

Dissolution test using water Dissolved amount (μg/ml)

TABLE 58

| | Elution time (min) | | | | |
|---|---|---|---|---|---|
| Example No. | 3 | 10 | 30 | 120 | 360 |
| Example 29 | 543.8 | 608.4 | 642.8 | 664.6 | 985.2 |
| Comparative Example 29 | 108.1 | 120.8 | 126.4 | 180.1 | 302.4 |

Dissolution test using 2nd fluid for disintegration test Dissolved amount (μg/ml)

TABLE 59

| | Elution time (min) | | | | |
|---|---|---|---|---|---|
| Example No. | 3 | 10 | 30 | 120 | 360 |
| Example 29 | 2097.5 | 2191.5 | 2206.7 | 2523.1 | 2524.6 |
| Comparative Example 29 | 2001.7 | 2061.7 | 2129.3 | 2102.5 | 2107.4 |

26. Isosorbide Dinitrate

Dissolution test using water Dissolved amount (μg/ml)

TABLE 60

| | Elution time (min) | | | | |
|---|---|---|---|---|---|
| Example No. | 3 | 10 | 30 | 120 | 360 |
| Example 30 | 14700.3 | 14719.3 | 14750.7 | 14860.5 | 15343.4 |
| Comparative Example 30 | 3465.7 | 3393.1 | 3490.4 | 3516.8 | 3466.0 |

Dissolution test using 2nd fluid for disintegration test Dissolved amount (μg/ml)

TABLE 61

| | Elution time (min) | | | | |
|---|---|---|---|---|---|
| Example No. | 3 | 10 | 30 | 120 | 360 |
| Example 30 | 33211.5 | 33051.8 | 32859.9 | 33084.0 | 33761.9 |
| Comparative Example 30 | 7156.8 | 7154.4 | 7134.1 | 7236.5 | 7148.8 |

27. Dipyridamole

Dissolution test using water Dissolved amount (μg/ml)

TABLE 62

| | Elution time (min) | | | | |
|---|---|---|---|---|---|
| Example No. | 3 | 10 | 30 | 120 | 360 |
| Example 31 | 85.2 | 94.8 | 146.1 | 154.5 | 142.3 |
| Comparative Example 31 | 7.8 | 7.9 | 8.0 | 8.5 | 8.2 |

Dissolution test using 2nd fluid for disintegration test Dissolved amount (μg/ml)

TABLE 63

| | Elution time (min) | | | | |
|---|---|---|---|---|---|
| Example No. | 3 | 10 | 30 | 120 | 360 |
| Example 31 | 31.8 | 60.9 | 88.1 | 53.8 | 55.6 |
| Comparative Example 31 | 6.5 | 6.5 | 8.3 | 8.5 | 9.2 |

28. Gliclazide

Dissolution test using water Dissolved amount (μg/ml)

TABLE 64

| | Elution time (min) | | | | |
|---|---|---|---|---|---|
| Example No. | 3 | 10 | 30 | 120 | 360 |
| Example 32 | 3460.7 | 3474.9 | 3505.2 | 3601.1 | 3683.8 |
| Comparative Example 32 | 11.1 | 26.3 | 35.4 | 38.8 | 39.3 |

Dissolution test using 2nd fluid for disintegration test Dissolved amount (μg/ml)

TABLE 65

| | Elution time (min) | | | | |
|---|---|---|---|---|---|
| Example No. | 3 | 10 | 30 | 120 | 360 |
| Example 32 | 1989.9 | 2041.1 | 2192.1 | 2100.5 | 1607.8 |
| Comparative Example 32 | 80.1 | 206.1 | 296.1 | 420.2 | 429.4 |

29. Metoclopramide
Dissolution test using water Dissolved amount (μg/ml)

TABLE 66

| Example No. | Elution time (min) | | | | |
|---|---|---|---|---|---|
| | 3 | 10 | 30 | 120 | 360 |
| Example 33 | 16990.8 | 18151.5 | 17184.4 | 17227.2 | 17330.8 |
| Comparative Example 33 | 6159.5 | 5382.3 | 5437.6 | 5478.0 | 5654.9 |

Dissolution test using 2nd fluid for disintegration test Dissolved amount (μg/ml)

TABLE 67

| Example No. | Elution time (min) | | | | |
|---|---|---|---|---|---|
| | 3 | 10 | 30 | 120 | 360 |
| Example 33 | 42654.9 | 43463.8 | 42088.2 | 43344.2 | 44893.5 |
| Comparative Example 33 | 12420.8 | 13825.3 | 13285.5 | 13534.7 | 13564.1 |

30. Spironolactone
Dissolution test using water Dissolved amount (μg/ml)

TABLE 68

| Example No. | Elution time (min) | | | | |
|---|---|---|---|---|---|
| | 3 | 10 | 30 | 120 | 360 |
| Example 34 | 64.0 | 63.9 | 65.6 | 70.1 | 101.3 |
| Comparative Example 34 | 29.6 | 31.9 | 33.7 | 39.7 | 35.2 |

Dissolution test using 2nd fluid for disintegration test Dissolved amount (μg/ml)

TABLE 69

| Example No. | Elution time (min) | | | | |
|---|---|---|---|---|---|
| | 3 | 10 | 30 | 120 | 360 |
| Example 34 | 185.0 | 157.8 | 123.6 | 135.0 | 138.0 |
| Comparative Example 34 | 71.0 | 85.6 | 89.3 | 92.0 | 93.7 |

31. Furosemide
Dissolution test using water Dissolved amount (μg/ml)

TABLE 70

| Example No. | Elution time (min) | | | | |
|---|---|---|---|---|---|
| | 3 | 10 | 30 | 120 | 360 |
| Example 35 | 5775.3 | 6147.0 | 6195.7 | 6181.7 | 6168.6 |
| Comparative Example 35 | 32.1 | 36.6 | 40.7 | 35.3 | 30.5 |

Dissolution test using 2nd fluid for disintegration test Dissolved amount (μg/ml)

TABLE 71

| Example No. | Elution time (min) | | | | |
|---|---|---|---|---|---|
| | 3 | 10 | 30 | 120 | 360 |
| Example 35 | 10880.7 | 11509.3 | 11395.9 | 11345.2 | 11100.3 |
| Comparative Example 35 | 1789.1 | 1773.6 | 1768.6 | 1860.3 | 1924.2 |

32. Mefenamic acid
Dissolution test using water Dissolved amount (μg/ml)

TABLE 72

| Example No. | Elution time (min) | | | | |
|---|---|---|---|---|---|
| | 3 | 10 | 30 | 120 | 360 |
| Example 36 | 2259.4 | 2422.5 | 2284.4 | 2214.0 | 1816.0 |
| Example 36 | 0.8 | 3.1 | 5.3 | 5.2 | 4.5 |

Dissolution test using 2nd fluid for disintegration test Dissolved amount (μg/ml)

TABLE 73

| Example No. | Elution time (min) | | | | |
|---|---|---|---|---|---|
| | 3 | 10 | 30 | 120 | 360 |
| Example 36 | 668.4 | 417.9 | 370.0 | 268.8 | 252.1 |
| Example 36 | 10.0 | 32.4 | 39.6 | 46.0 | 56.6 |

33. Nifedipine
Dissolution test using water Dissolved amount (μg/ml)

TABLE 74

| Example No. | Elution time (min) | | | | |
|---|---|---|---|---|---|
| | 3 | 10 | 30 | 120 | 360 |
| Example 37 | 44.1 | 72.5 | 66.8 | 117.0 | 160.5 |
| Comparative Example 37 | 7.9 | 8.9 | 9.0 | 10.9 | 15.3 |

Dissolution test using 2nd fluid for disintegration test Dissolved amount (μg/ml)

TABLE 75

| Example No. | Elution time (min) | | | | |
|---|---|---|---|---|---|
| | 3 | 10 | 30 | 120 | 360 |
| Example 37 | 88.9 | 119.0 | 121.4 | 104.2 | 79.2 |
| Comparative Example 37 | 9.9 | 12.7 | 12.2 | 12.8 | 18.0 |

34. Probenecid

Dissolution test using water Dissolved amount (μg/ml)

TABLE 76

| Example No. | Elution time (min) | | | | |
|---|---|---|---|---|---|
| | 3 | 10 | 30 | 120 | 360 |
| Example 38 | 8696.2 | 8687.9 | 8674.2 | 8668.8 | 8617.1 |
| Comparative Example 38 | 10.7 | 22.7 | 33.4 | 39.8 | 37.5 |

Dissolution test using 2nd fluid for disintegration test Dissolved amount (μg/ml)

TABLE 77

| Example No. | Elution time (min) | | | | |
|---|---|---|---|---|---|
| | 3 | 10 | 30 | 120 | 360 |
| Example 38 | 13428.7 | 13379.3 | 13353.6 | 13020.2 | 12851.1 |
| Comparative Example 38 | 386.2 | 1107.2 | 1315.0 | 2619.5 | 3715.9 |

35. Allopurinol

Dissolution test using water Dissolved amount (μg/ml)

TABLE 78

| Example No. | Elution time (min) | | | | |
|---|---|---|---|---|---|
| | 3 | 10 | 30 | 120 | 360 |
| Example 39 | 1469.6 | 1615.8 | 1639.4 | 1611.4 | 1497.4 |
| Comparative Example 39 | 578.2 | 679.4 | 773.9 | 741.5 | 712.5 |

Dissolution test using 2nd fluid for disintegration test Dissolved amount (μg/ml)

TABLE 79

| Example No. | Elution time (min) | | | | |
|---|---|---|---|---|---|
| | 3 | 10 | 30 | 120 | 360 |
| Example 39 | 984.7 | 1168.4 | 1121.5 | 1131.1 | 1154.2 |
| Comparative Example 39 | 565.4 | 672.6 | 725.7 | 722.8 | 696.1 |

36. Propylthiouracil

Dissolution test using water Dissolved amount (μg/ml)

TABLE 80

| Example No. | Elution time (min) | | | | |
|---|---|---|---|---|---|
| | 3 | 10 | 30 | 120 | 360 |
| Example 40 | 3836.3 | 3796.0 | 3772.6 | 3471.1 | 3561.9 |
| Comparative Example 40 | 432.6 | 443.9 | 927.7 | 1370.0 | 1490.0 |

Dissolution test using 2nd fluid for disintegration test Dissolved amount (μg/ml)

TABLE 81

| Example No. | Elution time (min) | | | | |
|---|---|---|---|---|---|
| | 3 | 10 | 30 | 120 | 360 |
| Example 40 | 2250.4 | 2470.2 | 2732.5 | 2458.7 | 2379.8 |
| Comparative Example 40 | 472.1 | 502.3 | 853.5 | 1412.6 | 1507.2 |

37. Prednisolone

Dissolution test using water Dissolved amount (μg/ml)

TABLE 82

| Example No. | Elution time (min) | | | | |
|---|---|---|---|---|---|
| | 3 | 10 | 30 | 120 | 360 |
| Example 41 | 761.0 | 760.7 | 765.4 | 741.0 | 755.8 |
| Comparative Example 41 | 356.0 | 336.3 | 315.8 | 268.2 | 266.3 |

Dissolution test using 2nd fluid for disintegration test Dissolved amount (μg/ml)

TABLE 83

| Example No. | Elution time (min) | | | | |
|---|---|---|---|---|---|
| | 3 | 10 | 30 | 120 | 360 |
| Example 41 | 801.9 | 825.4 | 806.3 | 772.8 | 726.5 |
| Comparative Example 41 | 369.1 | 382.4 | 310.8 | 265.5 | 257.9 |

38. Pindolol

Dissolution test using water Dissolved amount (μg/ml)

TABLE 84

| Example No. | Elution time (min) | | | | |
|---|---|---|---|---|---|
| | 3 | 10 | 30 | 120 | 360 |
| Example 42 | 454.9 | 379.7 | 410.7 | 571.8 | 656.2 |
| Comparative Example 42 | 53.1 | 71.1 | 77.8 | 93.5 | 93.6 |

Dissolution test using 2nd fluid for disintegration test Dissolved amount (μg/ml)

TABLE 85

| Example No. | Elution time (min) | | | | |
|---|---|---|---|---|---|
| | 3 | 10 | 30 | 120 | 360 |
| Example 42 | 2625.6 | 3583.1 | 3552.6 | 4204.6 | 3921.1 |
| Comparative Example 42 | 1394.9 | 2837.9 | 3212.1 | 3624.7 | 3387.5 |

39. Rifampicin

Dissolution test using water Dissolved amount (μg/ml)

TABLE 86

| Example No. | Elution time (min) | | | | |
|---|---|---|---|---|---|
| | 3 | 10 | 30 | 120 | 360 |
| Example 43 | 2269.8 | 1876.3 | 2015.1 | 2062.5 | 2144.8 |
| Comparative Example 43 | 137.7 | 248.5 | 392.0 | 476.4 | 533.3 |

Dissolution test using 2nd fluid for disintegration test Dissolved amount (μg/ml)

TABLE 87

| Example No. | Elution time (min) | | | | |
|---|---|---|---|---|---|
| | 3 | 10 | 30 | 120 | 360 |
| Example 43 | 1150.8 | 1193.3 | 1189.7 | 1198.9 | 1158.6 |
| Comparative Example 43 | 128.3 | 250.6 | 349.6 | 545.9 | 836.0 |

40. Estradiol Enanthate

Dissolution test using water Dissolved amount (μg/ml)

TABLE 88

| Example No. | Elution time (min) | | | | |
|---|---|---|---|---|---|
| | 3 | 10 | 30 | 120 | 360 |
| Example 44 | 7.6 | 7.9 | 7.5 | 8.1 | 13.5 |
| Comparative Example 44 | 1.6 | 1.4 | 1.8 | 1.6 | 1.3 |

Dissolution test using 2nd fluid for disintegration test Dissolved amount (μg/ml)

TABLE 89

| Example No. | Elution time (min) | | | | |
|---|---|---|---|---|---|
| | 3 | 10 | 30 | 120 | 360 |
| Example 44 | 56.1 | 133.2 | 374.7 | 129.6 | 133.6 |
| Comparative Example 44 | 7.9 | 10.2 | 7.0 | 19.0 | 10.9 |

41. Adenine

Dissolution test using water Dissolved amount (μg/ml)

TABLE 90

| Example No. | Elution time (min) | | | | |
|---|---|---|---|---|---|
| | 3 | 10 | 30 | 120 | 360 |
| Example 45 | 3106.8 | 3251.1 | 3154.5 | 3038.0 | 2748.8 |
| Comparative Example 45 | 1478.0 | 1557.3 | 1646.6 | 1657.8 | 1696.4 |

Dissolution test using 2nd fluid for disintegration test Dissolved amount (μg/ml)

TABLE 91

| Example No. | Elution time (min) | | | | |
|---|---|---|---|---|---|
| | 3 | 10 | 30 | 120 | 360 |
| Example 45 | 2841.8 | 2752.3 | 2831.6 | 2485.2 | 2343.3 |
| Comparative Example 45 | 1752.2 | 2028.0 | 2001.9 | 2001.4 | 1876.8 |

42. Haloperidol

Dissolution test using water Dissolved amount (μg/ml)

TABLE 92

| Example No. | Elution time (min) | | | | |
|---|---|---|---|---|---|
| | 3 | 10 | 30 | 120 | 360 |
| Example 46 | 14.9 | 15.4 | 15.6 | 16.0 | 16.4 |
| Comparative Example 46 | 8.2 | 10.0 | 11.3 | 12.8 | 13.1 |

Dissolution test using 2nd fluid for disintegration test Dissolved amount (μg/ml)

TABLE 93

| Example No. | Elution time (min) | | | | |
|---|---|---|---|---|---|
| | 3 | 10 | 30 | 120 | 360 |
| Example 46 | 87.1 | 103.2 | 120.5 | 115.8 | 107.1 |
| Comparative Example 46 | 23.9 | 35.6 | 45.2 | 50.1 | 48.9 |

43. Lidocaine

Dissolution test using water Dissolved amount (μg/ml)

TABLE 94

| Example No. | Elution time (min) | | | | |
|---|---|---|---|---|---|
| | 3 | 10 | 30 | 120 | 360 |
| Example 47 | 2769.1 | 3319.6 | 3799.3 | 4627.3 | 5085.4 |
| Comparative Example 47 | 2413.8 | 3261.4 | 3557.3 | 3732.5 | 3759.7 |

Dissolution test using 2nd fluid for disintegration test Dissolved amount (μg/ml)

TABLE 95

| Example No. | Elution time (min) | | | | |
|---|---|---|---|---|---|
| | 3 | 10 | 30 | 120 | 360 |
| Example 47 | 5825.8 | 7936.4 | 8903.1 | 9763.3 | 10760.0 |
| Comparative Example 47 | 1873.3 | 2931.4 | 4039.8 | 5485.0 | 5469.0 |

44. Sulpiride
Dissolution test using water Dissolved amount (μg/ml)

TABLE 96

| | Elution time (min) | | | | |
|---|---|---|---|---|---|
| Example No. | 3 | 10 | 30 | 120 | 360 |
| Example 48 | 1146.0 | 1204.8 | 1184.8 | 1373.1 | 1344.8 |
| Comparative Example 48 | 555.2 | 772.8 | 803.2 | 724.9 | 715.8 |

Dissolution test using 2nd fluid for disintegration test Dissolved amount (μg/ml)

TABLE 97

| | Elution time (min) | | | | |
|---|---|---|---|---|---|
| Example No. | 3 | 10 | 30 | 120 | 360 |
| Example 48 | 6538.8 | 7098.0 | 7944.4 | 8170.0 | 8459.8 |
| Comparative Example 48 | 5873.2 | 6995.7 | 6751.4 | 7206.2 | 6866.1 |

45. Carvedilol
Dissolution test using water Dissolved amount (μg/ml)

TABLE 98

| | Elution time (min) | | | | |
|---|---|---|---|---|---|
| Example No. | 3 | 10 | 30 | 120 | 360 |
| Example 49 | 14.6 | 20.0 | 23.8 | 27.9 | 28.2 |
| Comparative Example 49 | 5.2 | 8.3 | 10.0 | 15.0 | 16.0 |

Dissolution test using 2nd fluid for disintegration test Dissolved amount (μg/ml)

TABLE 99

| | Elution time (min) | | | | |
|---|---|---|---|---|---|
| Example No. | 3 | 10 | 30 | 120 | 360 |
| Example 49 | 22.2 | 33.3 | 53.7 | 59.7 | 59.2 |
| Comparative Example 49 | 13.9 | 26.3 | 48.6 | 44.1 | 45.1 |

In addition to the aforementioned substances, the same test was carried out on the following poorly-soluble substances: ibuprofen, clemastine fumarate, diazepam, trichlorocarbanilide, etoxazole, atrazine, ceftazidime, cefmenoxime hydrochloride, aztreonam, nystatin, amoxapine, methyldopa, valsartan, alprostadil alfadex, palux, L-carbocysteine, sucralfate, trimebutine maleate, salazosulfapyridine, argatroban, ethyl icosapentate, methylprednisolone, estradiol benzoate, estradiol valerate, estriol, hydroxyprogesterone caproate, cyclosporine, tacrolimus hydrate, dacarbazine, docetaxel hydrate, and paclitaxel. As a result, in all cases of the aforementioned poorly-soluble substances, a solubility-improving effect was obtained.

Moreover, a comparative test was carried out using silica fume instead of the calcium compound microparticles. Specifically, a coating treatment was carried out according to the same method as that described in the above section "6-1. For use in Examples [Coating of poorly-soluble substance with calcium compound microparticles according to Mechanofusion System]," using aspirin as a poorly-soluble substance, and using silica fume with a particle size of approximately 0.15 μm (TOMOE Engineering Co., Ltd.), instead of using the calcium compound microparticles.

As a result of measuring the "dissolved amount after dissolution test for 360 minutes" of this coated substance, the dissolved amount of the substance in distilled water was found to be 1676.2 μg/ml, and the dissolved amount of the substance in 2nd fluid for disintegration test was found to be 1740.2 μg/ml. Thus, the obtained dissolved amounts were lower than the dissolved amount of aspirin as a single use in distilled water (3110.4 μg/ml) and the dissolved amount of aspirin as a single use in 2nd fluid for disintegration test (6552.7 μg/ml). Accordingly, a solubility-improving effect was not obtained in the comparative test.

The invention claimed is:

1. A method for producing a substance with improved aqueous solubility, which comprises coating a surface of a poorly-soluble substance particle with calcium compound microparticles,
   wherein the poorly-soluble substance is a food additive or an active ingredient in a product selected from the group consisting of a pharmaceutical product, a veterinary pharmaceutical product, a quasi-drug, a cosmetic product, and an agricultural chemical product, and
   wherein the surface of the poorly-soluble substance particle is coated by applying mechanical energy to allow the calcium compound microparticles to penetrate into the poorly-soluble substance particle.

2. The method for producing a substance with improved aqueous solubility according to claim 1, wherein the calcium compound is calcium phosphate or calcium carbonate.

3. The method for producing a substance with improved aqueous solubility according to claim 2, wherein the calcium phosphate is hydroxyapatite or tricalcium phosphate.

4. The method for producing a substance with improved aqueous solubility according to any one of claims 1 to 3, wherein at least 5% of the surface of the poorly-soluble substance particle is coated with the calcium compound microparticles.

5. The method for producing a substance with improved aqueous solubility according to claim 1, wherein the method of applying mechanical energy comprises mechanical fusion.

6. The method for producing a substance with improved aqueous solubility according to claim 1, wherein the method of applying mechanical energy comprises hybridization.

7. The method for producing a substance with improved aqueous solubility according to claim 1, wherein a mean particle size of the calcium compound microparticles is 100 μm or less.

8. The method for producing a substance with improved aqueous solubility according to claim 1, wherein the specific surface area of the calcium compound microparticles is 20 $m^2$/g or more.

9. The method for producing a substance with improved aqueous solubility according to claim 1, wherein the calcium compound microparticles are microparticles coated with a dispersing agent.

10. The method for producing a substance with improved aqueous solubility according to claim 9, wherein the dispersing agent is at least one selected from the group consisting of citric acid, citrate, pyrophosphoric acid, and chondroitin sulfate.

11. The method for producing a substance with improved aqueous solubility according to claim 1, wherein the poorly-soluble substance is not resin or rubber.

\* \* \* \* \*